United States Patent
Oh et al.

(10) Patent No.: US 9,230,059 B2
(45) Date of Patent: Jan. 5, 2016

(54) MEDICAL IMAGING APPARATUS AND MEDICAL IMAGE MANAGEMENT METHOD

(71) Applicant: Samsung Electronics Co., Ltd., Suwon-si (KR)

(72) Inventors: Ki Jeong Oh, Bucheon-si (KR); Jong Hyun Shin, Seoul (KR); Woo Sup Han, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/467,298

(22) Filed: Aug. 25, 2014

(65) Prior Publication Data

US 2015/0063723 A1    Mar. 5, 2015

(30) Foreign Application Priority Data

Aug. 30, 2013 (KR) .................. 10-2013-0104492

(51) Int. Cl.
*G06K 9/00* (2006.01)
*G06F 19/00* (2011.01)

(52) U.S. Cl.
CPC .......... *G06F 19/321* (2013.01); *G06F 19/3406* (2013.01)

(58) Field of Classification Search
USPC .......... 382/128, 305, 132, 133, 239; 235/454, 235/455, 461; 345/637; 358/474; 271/264, 271/3.14; 375/E7.14, E7.16, 240.15; 704/262, 264
See application file for complete search history.

(56) References Cited

U.S. PATENT DOCUMENTS

| | | | |
|---|---|---|---|
| 5,786,817 A | 7/1998 | Sakano et al. | ................. 345/339 |
| 7,170,532 B2 * | 1/2007 | Sako | ..................... G06T 7/0012 |
| | | | 345/637 |
| 8,284,198 B1 | 10/2012 | Hackworth et al. | .......... 345/440 |
| 9,014,456 B2 * | 4/2015 | El-Baz | .................. G06K 9/621 |
| | | | 382/133 |

FOREIGN PATENT DOCUMENTS

| | | |
|---|---|---|
| DE | 102007040838 | 3/2009 |
| EP | 1176538 | 1/2002 |
| KR | 10-0647371 | 11/2006 |
| KR | 10-2007-0079208 | 8/2007 |

OTHER PUBLICATIONS

Extended European Search Report dated Jul. 9, 2015 in European Patent Application No. 14182254.4, 10 pages.

(Continued)

*Primary Examiner* — Anh Do
(74) *Attorney, Agent, or Firm* — Staas & Halsey LLP

(57) ABSTRACT

A medical imaging apparatus and a medical image management method provide information regarding image deletion to a user upon deleting stored images, thus allowing the user to intuitively recognize a storage capacity and to select a data capacity to be deleted. The medical imaging apparatus includes a storage unit storing images, a controller calculating a residual capacity among the storage capacity of the storage unit and determining whether or the residual capacity is less than a predetermined reference value, and a display unit displaying an auto deletion popup window receiving setting regarding a reference date for deletion of the stored images, if the residual capacity is less than the predetermined reference value.

32 Claims, 23 Drawing Sheets

(56) References Cited

OTHER PUBLICATIONS

"Description of the Low Disk Space Notification in Windows XP", Microsoft Support, Oct. 29, 2009, Article ID 285107, 3 pages.

"Automating Disk Cleanup Tools in Windows", Microsoft Support, Dec. 17, 2012, Article ID 253597, 7 pages.

* cited by examiner

"YES" SELECTION

"YES" SELECTION

MEDICAL IMAGING APPARATUS AND MEDICAL IMAGE MANAGEMENT METHOD

CROSS-REFERENCE TO RELATED APPLICATIONS

This application claims the priority benefit of Korean Patent Application No. 10-2013-0104492, filed on Aug. 30, 2013 in the Korean Intellectual Property Office, the disclosure of which is incorporated herein by reference.

BACKGROUND

1. Field

The following description relates to a medical imaging apparatus which images the inside of an object and a medical image management method which manages images stored in the medical imaging apparatus.

2. Description of the Related Art

Medical imaging apparatuses are apparatuses which may image the inside of an object to be used in diagnosis, and include a radioactive imaging apparatus which applies radiation to an object and detects radiation transmitted through the object, a magnetic resonance imaging apparatus which locates an object within a magnetic field, applies high-frequency signals to an object, and receives magnetic resonance signals from the object, and an ultrasound imaging apparatus which transmits ultrasonic waves to an object and receives echo signals reflected by the object.

Acquired medical images are stored in a storage space within a medical imaging apparatus or a Picture Archiving and Communication System (PACS) which manages medical images throughout a hospital. In order to prevent difficulty in storing acquired images due to insufficient storage capacity of the medical imaging apparatus or erroneous deletion of stored medical images, effective management of stored medical images based on user intention is required.

SUMMARY

Therefore, it is an aspect of the present disclosure to provide a medical imaging apparatus and a medical image management method which may provide information regarding medical image deletion to a user upon deleting stored medical images so that the user may intuitively recognize storage capacity and select a data capacity to be deleted.

Additional aspects of the disclosure will be set forth in part in the description which follows and, in part, will be obvious from the description, or may be learned by practice of the disclosure.

In accordance with an aspect of the present disclosure, a medical imaging apparatus includes a storage unit storing acquired medical images, a controller calculating a residual capacity among the storage capacity of the storage unit and determining whether or the residual capacity is less than a predetermined reference value, and a display unit displaying an auto deletion popup window receiving setting regarding a reference date for deletion of the stored medical images, if the residual capacity is less than the predetermined reference value.

The auto deletion popup window may include a plurality of period setup buttons corresponding to periods determining the reference date for deletion.

The controller, if one of the plurality of period setup buttons is selected, may determine the reference date for deletion based on the selected period setup button and the display unit may display the determined reference date for deletion on the auto deletion popup window.

The display unit may display information regarding the total storage capacity and current residual capacity of the storage unit on the auto deletion popup window.

The information regarding the total storage capacity and current residual capacity of the storage unit may include the maximum number of storable medical images or a numerical value displayed as a unit representing a storage capacity.

The display unit may display information regarding the currently used capacity of the storage unit on the auto deletion popup window.

The information regarding the currently used capacity of the storage unit may be displayed as a guide bar having a length proportional to the currently used capacity.

The display unit may display the guide bar in different colors according to currently used capacities.

The controller may calculate a used capacity and a residual capacity after deletion of medical images being a target to be deleted among the medical images stored in the storage unit, if the reference date for deletion is set.

The display unit may display information regarding the used capacity and residual capacity after deletion on the auto deletion popup window.

The information regarding the used capacity after deletion may be displayed as a guide bar having a length proportional to the used capacity after deletion.

The display unit may display the guide bar in different colors according to used capacities after deletion.

The controller may delete medical images acquired prior to the set reference date for deletion among the medical images stored in the storage unit, if a confirmation command regarding auto deletion is input.

The controller may determine whether or not there is any medical image corresponding to a deletion exception condition among the medical images acquired prior to the set reference date for deletion.

The deletion exception condition may include at least one of whether or not medical images are sent to a picture archiving and communication system (PACS), whether or not medical images are printed, whether or not approval messages are received from the PACS, and whether or not a lock of medical images is set.

In accordance with an aspect of the present disclosure, a medical image management method includes storing acquired medical images in a storage unit, calculating a residual capacity of the storage unit and determining whether or the residual capacity is less than a predetermined reference value, and displaying an auto deletion popup window receiving setting regarding a reference date for deletion of the stored medical images, if the residual capacity is less than the predetermined reference value.

The auto deletion popup window may include a plurality of period setup buttons corresponding to periods determining the reference date for deletion.

The medical image management method may further include, if one of the plurality of period setup buttons is selected, determining the reference date for deletion based on the selected period setup button, and displaying the determined reference date for deletion on the auto deletion popup window.

The auto deletion popup window may include information regarding the total storage capacity and current residual capacity of the storage unit.

The information regarding the total storage capacity and current residual capacity of the storage unit may include the maximum number of storable medical images or a numerical value displayed as a unit representing a storage capacity.

The auto deletion popup window may include information regarding the currently used capacity of the storage unit.

The information regarding the currently used capacity of the storage unit may be displayed as a guide bar having a length proportional to the currently used capacity.

The guide bar may be expressed in different colors according to currently used capacities.

The method image management method may further include calculating a used capacity and a residual capacity after deletion of medical images being a target to be deleted among the medical images stored in the storage unit, if the reference date for deletion is set.

The medical image management method may further include displaying information regarding the used capacity and residual capacity after deletion on the auto deletion popup window.

The information regarding the used capacity after deletion may be displayed as a guide bar having a length proportional to the used capacity after deletion.

The guide bar may be expressed in different colors according to used capacities after deletion.

The medical image management method may further include deleting medical images acquired prior to the set reference date for deletion among the medical images stored in the storage unit, if a confirmation command regarding auto deletion is input.

The medical image management method may further include determining whether or not there is any medical image corresponding to a deletion exception condition among the medical images acquired prior to the set reference date for deletion.

The deletion exception condition may include at least one of whether or not medical images are sent to a picture archiving and communication system (PACS), whether or not medical images are printed, whether or not approval messages are received from the PACS, and whether or not a lock of medical images is set.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
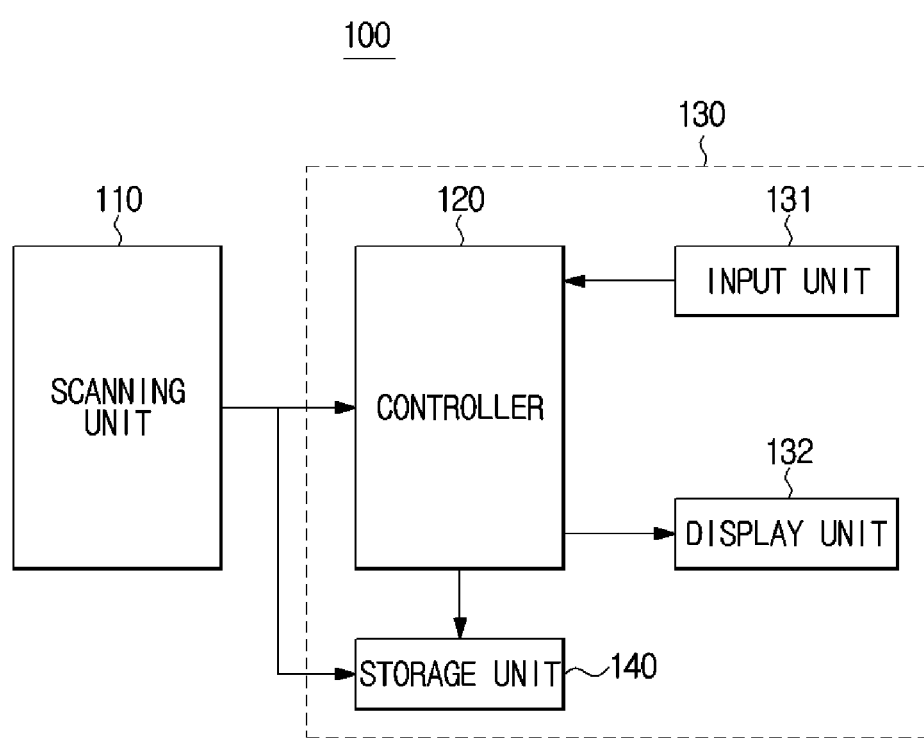
FIG. 1 is a control block diagram of a medical imaging apparatus in accordance with an embodiment of the present disclosure.

Reference will now be made in detail to the embodiments of the present disclosure, examples of which are illustrated in the accompanying drawings, wherein like reference numerals refer to like elements throughout.

FIG. 1 is a control block diagram of a medical imaging apparatus in accordance with an embodiment of the present disclosure.

With reference to FIG. 1, a medical imaging apparatus 100 in accordance with an embodiment of the present disclosure includes a scanning unit 110 acquiring an image of the inside of an object by scanning the object, a storage unit 140 storing the acquired image, a controller 120 managing images stored in the storage unit 140, an input unit 131 receiving a command regarding management of stored images from a user, and a display unit 132 displaying information for image management.

The controller 120, the storage unit 140, the input unit 131, and the display unit 132 may be provided in a workstation 130. The workstation 130 may be called a host apparatus or a console but is not limited thereto, and may be any apparatus which stores and manages medical images acquired by the medical imaging apparatus 100. In this embodiment of the present disclosure, the workstation 130 will be stated for convenience of description.

Figure 2A:
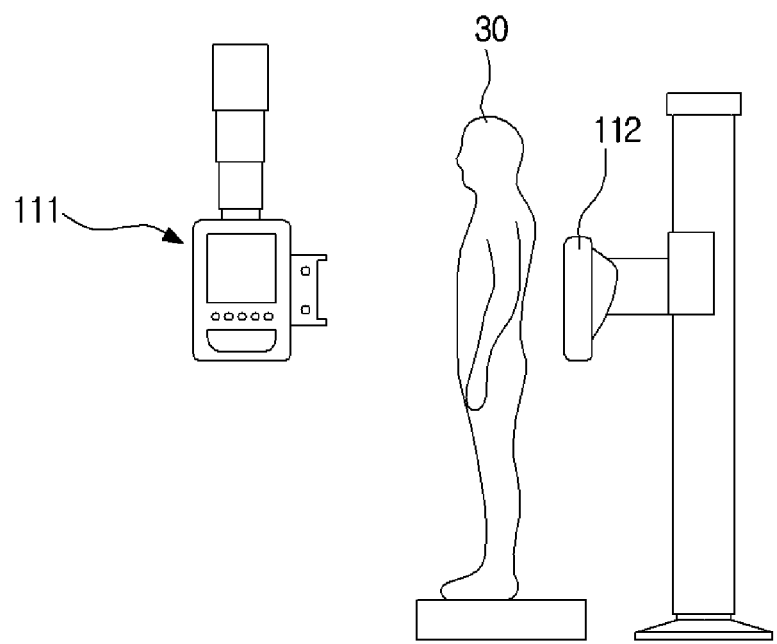
FIG. 2A is a view illustrating the external appearance of an X-ray imaging apparatus performing radiography as an example of the medical imaging apparatus.
Figure 2B:
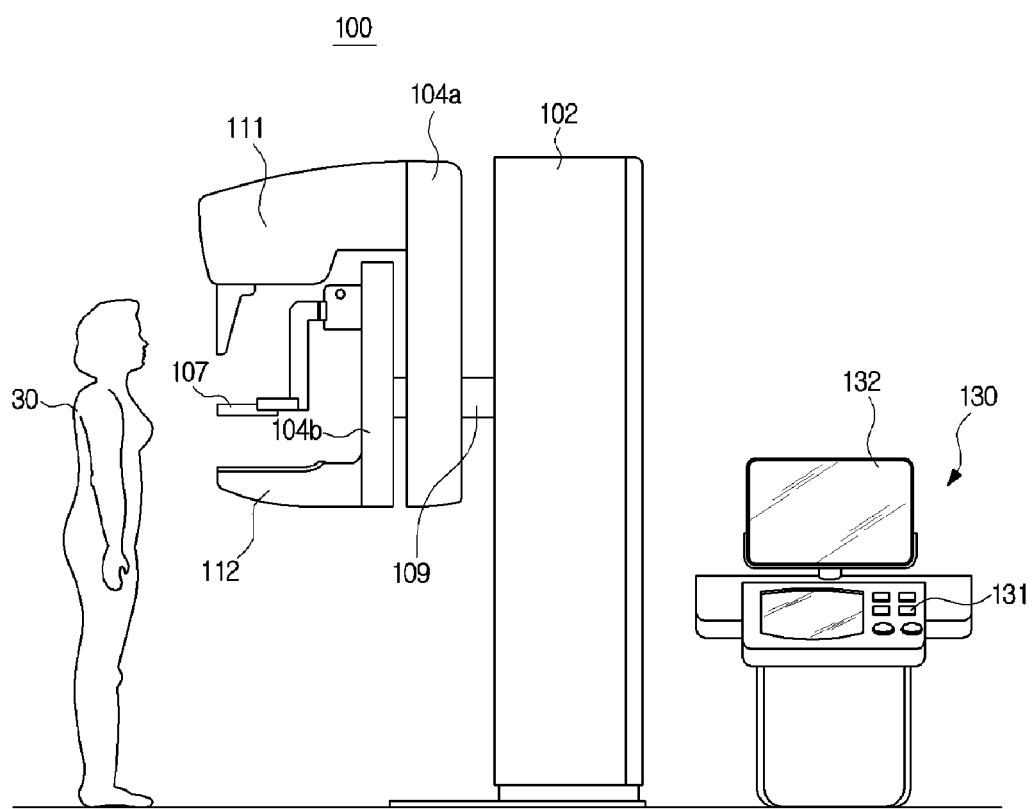
FIG. 2B is a view illustrating the external appearance of an X-ray imaging apparatus performing mammography as an example of the medical imaging apparatus.
Figure 2C:
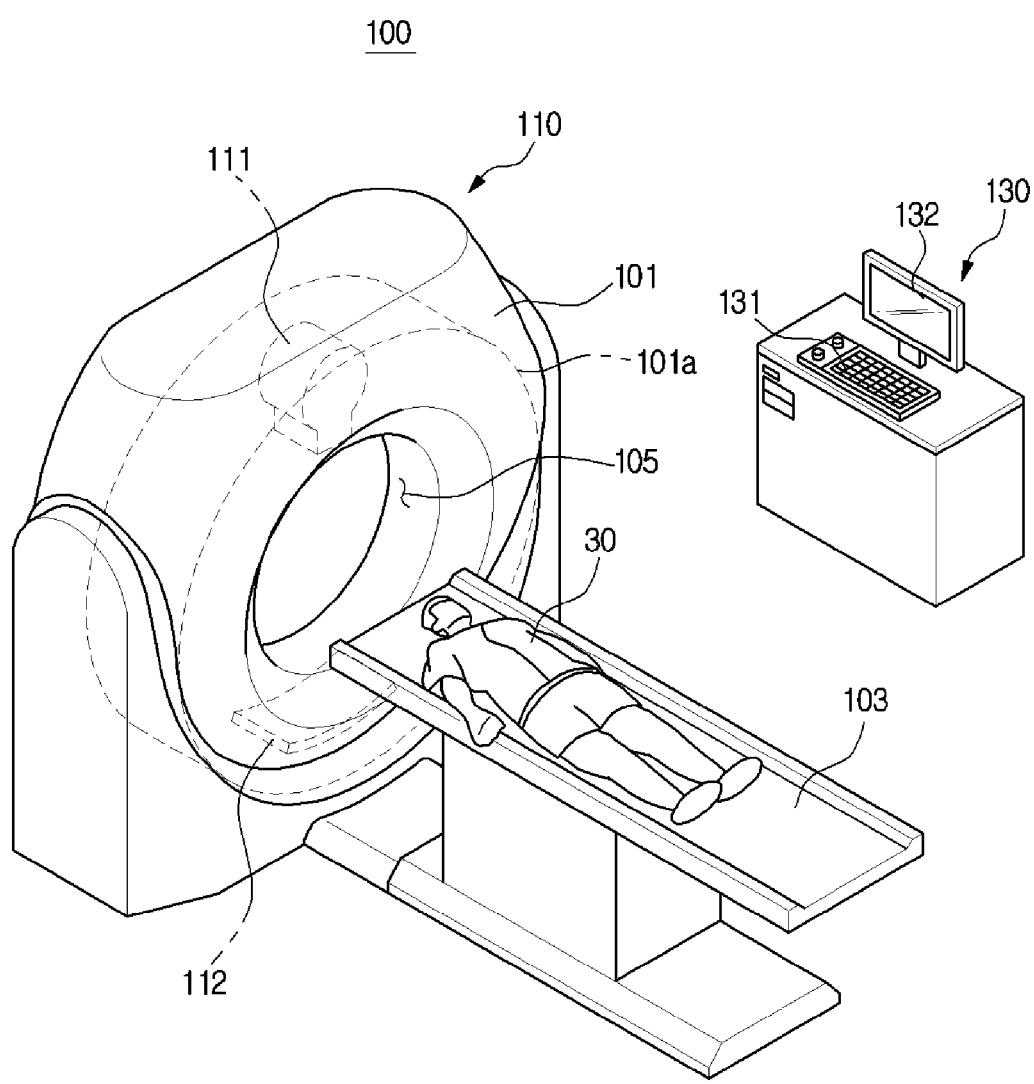
FIG. 2C is a perspective view illustrating the external appearance of a computed tomography (CT) apparatus as an example of the medical imaging apparatus.
Figure 2D:
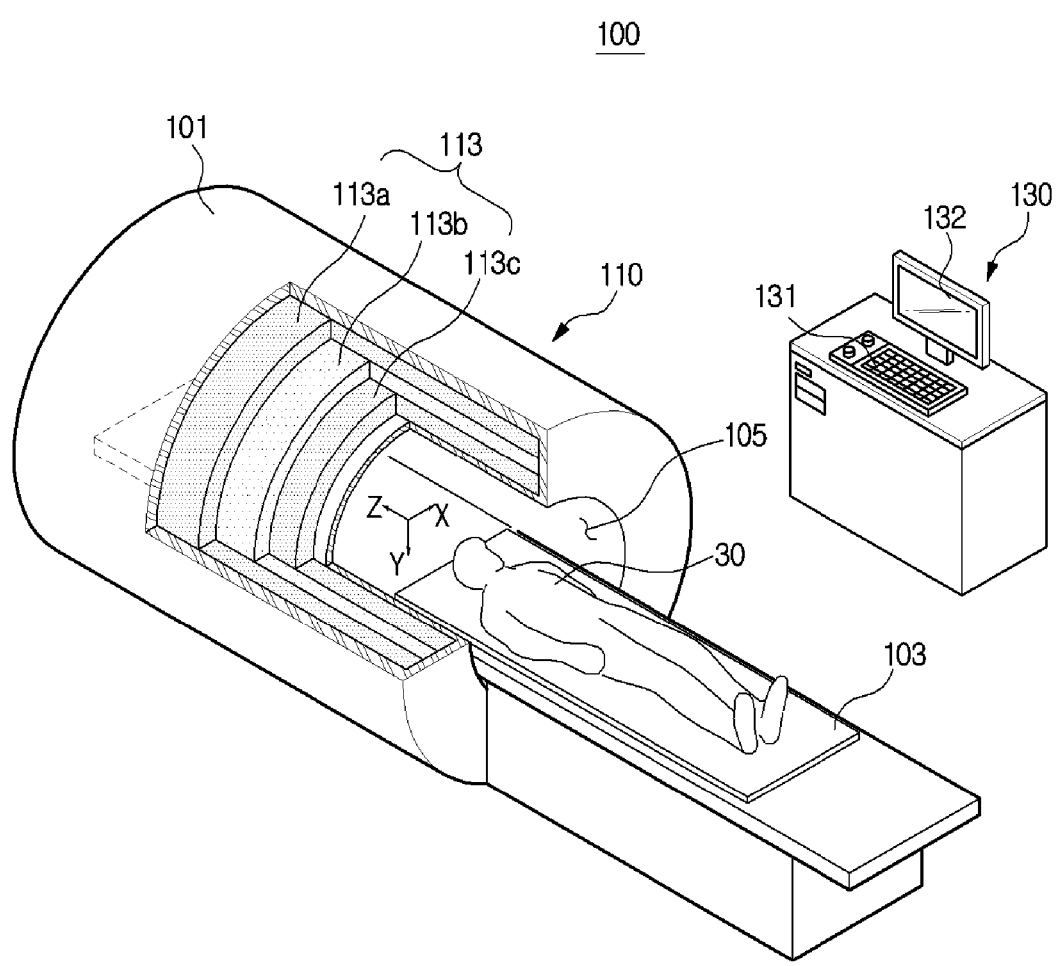
FIG. 2D is a perspective view illustrating the external appearance of a magnetic resonance imaging (MRI) apparatus as yet an example of the medical imaging apparatus.

FIG. 2A is a view illustrating the external appearance of an X-ray imaging apparatus performing radiography as an example of the medical imaging apparatus, FIG. 2B is a view illustrating the external appearance of an X-ray imaging apparatus performing mammography as an example of the medical imaging apparatus, FIG. 2C is a perspective view illustrating the external appearance of a computed tomography (CT) apparatus as an example of the medical imaging apparatus, and FIG. 2D is a perspective view illustrating the external appearance of a magnetic resonance imaging (MRI) apparatus as yet an example of the medical imaging apparatus.

The embodiment of the present disclosure may be applied to various kinds of medical imaging apparatuses. As an example, the embodiment of the present disclosure may be applied to an X-ray imaging apparatus which images the inside of an object by applying X-rays to the object and detecting X-rays transmitted through the object.

A general X-ray imaging technique to image most regions of a human body, such as the chest, the arms, and the legs, is referred to as radiography, and an X-ray imaging technique to image the breast of a human body is referred to as mammography. A technique to acquire an X-ray moving image is referred to fluoroscopy, and a technique to acquire a blood vessel image is referred to as angiography. X-ray imaging apparatuses may have slightly different structures according to the respective X-ray imaging techniques. Hereinafter, structures of X-ray imaging apparatuses performing radiography and mammography will be described with reference to FIGS. 2A and 2B.

If an X-ray imaging apparatus performing radiography is used as the medical imaging apparatus 100, as exemplarily shown in FIG. 2A, the X-ray imaging apparatus 100 includes an X-ray source 111 applying X-rays to an object 30 and an X-ray detector 112 detecting X-rays.

The X-ray source 111 is mounted on the ceiling of a room in which radiography is performed and applies X-rays to a region of the object 30 to be imaged, and the X-ray detector 112 detects X-rays transmitted through the object 30.

If an X-ray imaging apparatus performing mammography is used as the medical imaging apparatus 100, as exemplarily shown in FIG. 2B, an arm 104a is connected to a housing 102, an X-ray source 111 is mounted on the upper portion of the arm 104a, and an X-ray detector 112 is mounted on the lower portion of the arm 104a. If tomosynthesis is performed, the arm 104a may be rotated about a shaft 109.

The X-ray source 111 and the X-ray detector 112 are disposed opposite each other, X-rays are applied to the breast of an object 30 under the condition that the breast is located therebetween, and X-rays transmitted through the breast are detected. A compression paddle 107 is further provided on an arm 104b of the X-ray imaging apparatus 100 performing mammography in terms of characteristics of the breast consisting of soft tissues alone.

The compression paddle 107 serves to compress the breast to a designated thickness during X-ray imaging. When the breast is compressed, the thickness of the breast is decreased, an X-ray dosage may be reduced, a clearer image may be acquired, tissues overlapping each other are spread apart, and thus the inner structure of the breast may be more precisely observed.

A computed tomography (CT) apparatus acquires images using X-rays transmitted through an object in the same manner as the X-ray imaging apparatuses of FIGS. 2A and 2B, but differs from the X-ray imaging apparatuses of FIGS. 2A and 2B in that the computed tomography (CT) apparatus may acquire tomographic images of the object by applying X-rays to the object in different directions.

If a computed tomography (CT) apparatus is used as the medical imaging apparatus 100, as exemplarily shown in FIG. 2C, a gantry 101a is provided in a housing 101 of the scanning unit 110, and an X-ray source 111 and an X-ray detector 112 are disposed opposite each other within the gantry 101a.

When an object 30 is transferred by a patient table 103 and is located within a bore 105 at the center of the gantry 101a, the X-ray source 111 and the X-ray detector 112 are rotated by 360 degrees about the bore 105 and up to 128 images may be acquired during one rotation cycle. However, this is but one example and the number of acquired images may be varied according to slice thicknesses or channel numbers.

Although FIGS. 2A to 2C exemplarily illustrates the medical imaging apparatuses 100 using X-rays, an apparatus using other forms of radiation except for X-rays may be used as the medical imaging apparatus 100. For example, a positron emission tomography (PET) apparatus using gamma rays may be used as the medical imaging apparatus 100. The positron emission tomography (PET) apparatus images the inside of an object by injecting a drug containing a radioactive isotope emitting positrons into the body of the object and detecting gamma rays emitted due to annihilation of positrons emitted from the body.

Further, the medical imaging apparatus 100 may acquire magnetic resonance images. If a magnetic resonance imaging (MRI) apparatus is used as the medical imaging apparatus 100, as exemplarily shown in FIG. 2D, the scanning unit 110 includes a magnet assembly 113 mounted within a housing 101, and the magnet assembly 113 includes static magnetic field coils 113a forming a static magnetic field within a bore 105, gradient coils 113b forming gradient magnetic fields by generating gradients in the static magnetic field, and RF coils 113c exciting atomic nuclei by applying RF pulses to an object and receiving echo signals from the atomic nuclei.

That is, when a patient table 103 is transferred to the bore 105 in which a static magnetic field is formed, gradient magnetic fields and RF pulses are applied to an object 30 and thus atomic nuclei of the object 30 are excited and echo signals generated from the excited atomic nuclei are received and thus the inside of the object 30 is imaged.

Referring to FIGS. 2A to 2D again, the workstation 130 storing and managing images acquired by the scanning unit 110 is provided in each of the medical imaging apparatuses 100. The workstation 130 may be located in the same space as the scanning unit 110 or the scanning unit 110 may be placed in a shielding room and the workstation 130 may be placed in a separate user workspace.

In addition to the above-described examples, the medical imaging apparatus 100 may image the inside of an object by transmitting ultrasonic waves to the object and receiving echo signals reflected by the object. Further, any apparatus which may image the inside of an object to be used in diagnosis may be used as the medical imaging apparatus 100 in accordance with the embodiment of the present disclosure.

Figure 3:
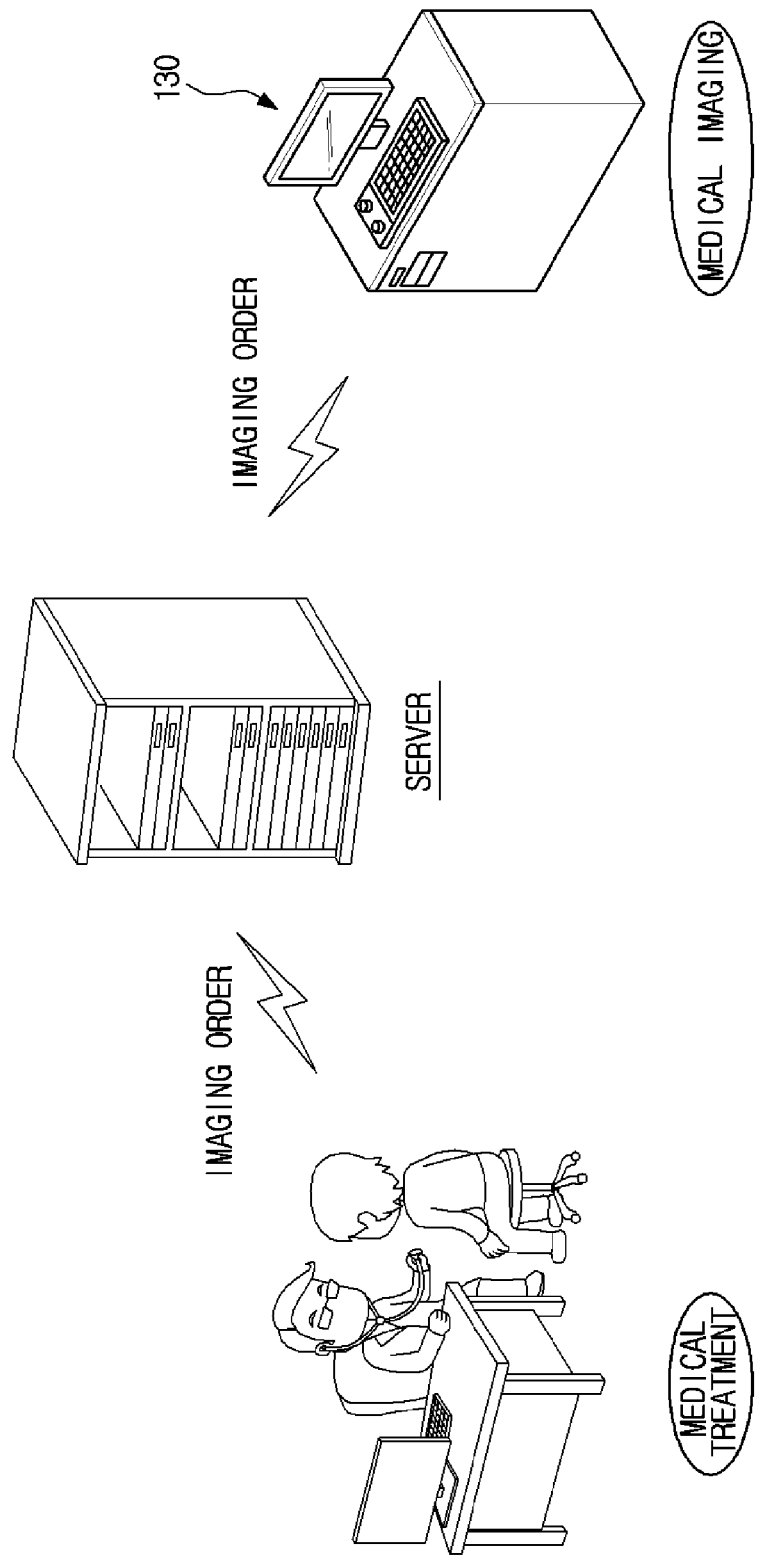
FIG. 3 is a view illustrating a process of receiving an order for medical imaging.
Figure 4:
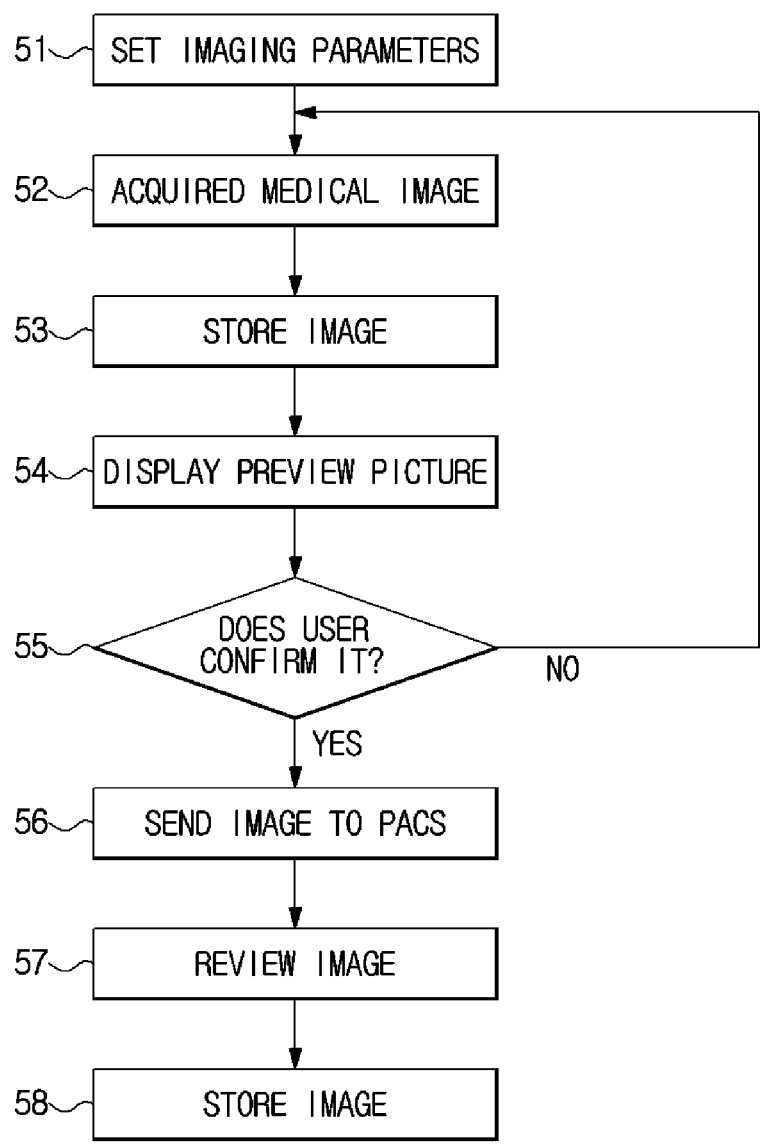
FIG. 4 is a flowchart illustrating a process of acquiring and storing medical images.

FIG. 3 is a view illustrating a process of receiving an order for medical imaging and FIG. 4 is a flowchart illustrating a process of acquiring and storing medical images.

The medical imaging apparatus 100 is used in a hospital or a health examination center. Hereinafter, a case that the medical imaging apparatus 100 is used in a hospital will be exemplarily described for convenience of description.

Further, although kinds of objects imaged by the medical imaging apparatus 100 are not limited, hereinafter, an object imaged by the medical imaging apparatus 100 will be referred to as a patient for convenience of description.

With reference to FIG. 3, a patient receives medical treatment from a doctor and describes symptoms or shows an affected part, and the doctor determines a region of the patient to be imaged according to the state of the patient and issues an imaging order. The imaging order issued by the doctor is transmitted to a server within the hospital, and the server transmits the imaging order issued by the doctor to the workstation 130 of the medical imaging apparatus 100 so that medical images may be acquired according to the imaging order.

For detailed description, a case that an X-ray imaging apparatus is used as the medical imaging apparatus 100 will be exemplarily described with reference to FIG. 4. A series of processes of medical imaging in a hospital may be divided into generation and transmission of a work list, acquisition of images, and review of the acquired images. The work list means the imaging order of the doctor, described in FIG. 3, and acquisition and review of images means imaging using the medical imaging apparatus 100 and work performed over acquired images. Such a process will be illustrated in FIG. 4.

When the imaging order is transmitted from the server of the hospital, as exemplarily shown in FIG. 4, imaging parameters may be set (Operation 51). The imaging parameters include exposure parameter, such as tube current, tube voltage, exposure time, filter kind, and anode material, and the imaging parameters may be preset or changed by a user. Here, the user means a subject performing imaging using the medical imaging apparatus 100, such as a radiologist.

When the imaging parameters are set, a medical image of a patient is acquired (Operation 52). Acquisition of the medical image is performed by the scanning unit 110, as exemplarily shown in FIGS. 2A to 2D, and the medical image acquired by the scanning unit 110 is transmitted to the workstation 130 and stored in the storage unit 140 (Operation 53). The storage unit 140 may be a memory device, such as a hard disk, a flash memory, or a ROM.

The acquired image is displayed as a preview picture (Operation 54). The preview picture is displayed on the display unit 132. When the user confirms the acquired image through the preview picture (Yes of Operation 55), the acquired image is transmitted to a picture archiving and communication system (PACS) of the hospital (Operation 56), and when the user does not confirm the acquired image, i.e., rejects confirmation of the acquired image (No of Operation 55), imaging is performed again.

The medical imaging apparatus 100 may perform an auto confirmation function. If the auto confirmation function is set, the acquired image may be transmitted to the PACS regardless of whether or not the user confirms the acquired image.

When the user confirms the acquired image, a review picture is displayed and the user performs review of the image through the displayed review picture (Operation 57). The user may amend the image through review, and the amended image is stored in the storage unit 140 (Operation 58). Further, the amended image may be transmitted to the PACS.

The PACS receives and stores medical images transmitted from plural plurality of medical imaging apparatuses 100 provided in the hospital, and transmits again the stored medical images to doctors in charge of corresponding patients so that the doctors may make diagnoses on states of the patients through the medical images.

As described above, both the medical image acquired by the scanning unit 110 and the medical image amended by the user may be stored in the storage unit 140. Because one medical imaging apparatus 100 is continuously used in the hospital and acquires and stores medical images of plural patients, effective management of the storage capacity of the storage unit 140 is required.

Figure 5:
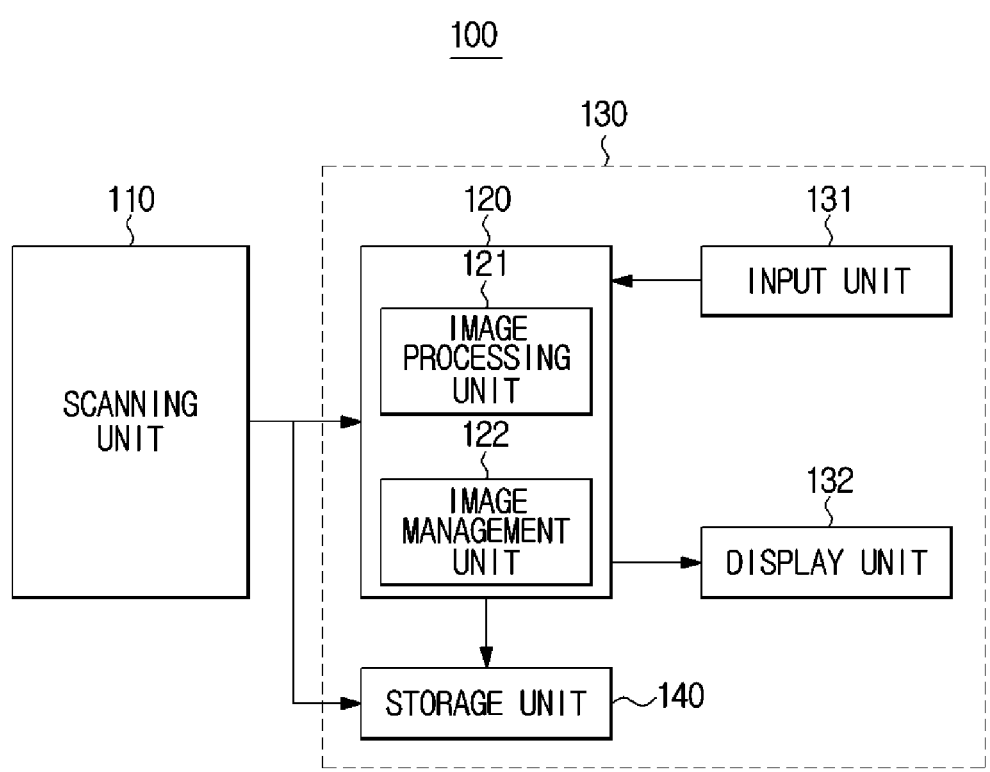
FIG. 5 is a control block diagram of a controller of the medical imaging apparatus in accordance with an embodiment of the present disclosure.

FIG. 5 is a control block diagram of the controller 120 of the medical imaging apparatus 100 in accordance with the embodiment of the present disclosure.

With reference to FIG. 5, the controller 120 includes an image processing unit 121 processing the image acquired by the scanning unit 110 and an image management unit 122 managing medical images stored in the storage unit 140.

The image acquired and transmitted by the scanning unit 110 is an original image consisting of raw data. For example, if the scanning unit 110 acquires an X-ray image, digital data representing a dose of X-rays incident upon each pixel of the X-ray detector 112 is transmitted to the workstation 130.

The original image may be excessively dark or bright and may not clearly distinguish inner parts of the patient. Therefore, the image processing unit 121 performs various kinds of processing of the image transmitted from the scanning unit 110 so that the image may be converted into a type readable by the user.

In general, the original image may be temporarily stored in the storage unit 140 and deleted after image processing. Storage and provision of the original image may be selected as an option by the user and the original image may be stored together with processed medical images by user selection.

The image management unit 122 manages medical images stored in the storage unit 140. In the embodiment of the present disclosure, medical images refer to all images acquired by the scanning unit 110 of the medical imaging apparatus 100 and include original images and processed images.

In more detail, the image management unit 122 may manage the storage capacity of the storage unit 140 by automatically deleting medical images stored in the storage unit 140. The image management unit 122 may execute medical image auto deletion if the residual capacity of the storage unit 140 is less than a predetermined reference value.

For this purpose, the image management unit 122 calculates the residual capacity, i.e., a capacity acquired by subtracting the capacity being used now (based on a point of time of calculation) from the total storage capacity of the storage unit 140, and compares the residual capacity with the set reference value. Calculation of the residual capacity and comparison between the residual capacity and the predetermined reference value may be performed upon booting the medical imaging apparatus 100 or logging in to the medical imaging apparatus 100, be performed when medical images are acquired after booting or logging in, and be periodically performed.

If auto deletion is executed, the image management unit 122 does not arbitrarily delete medical images stored in the storage unit 140, but receives a command regarding deletion from the user and then performs deletion according to the received command. That is, the image management unit 122 may execute auto deletion of medical images according to user command from an input unit 131, and thus prevent unintended deletion of medical images by the user.

For this purpose, the image management unit 122 controls the display unit 132 to display a popup window providing information regarding the storage capacity of the storage unit 140 and guiding input of a command regarding deletion so that the user may input the command regarding deletion of medical images.

Figure 6:
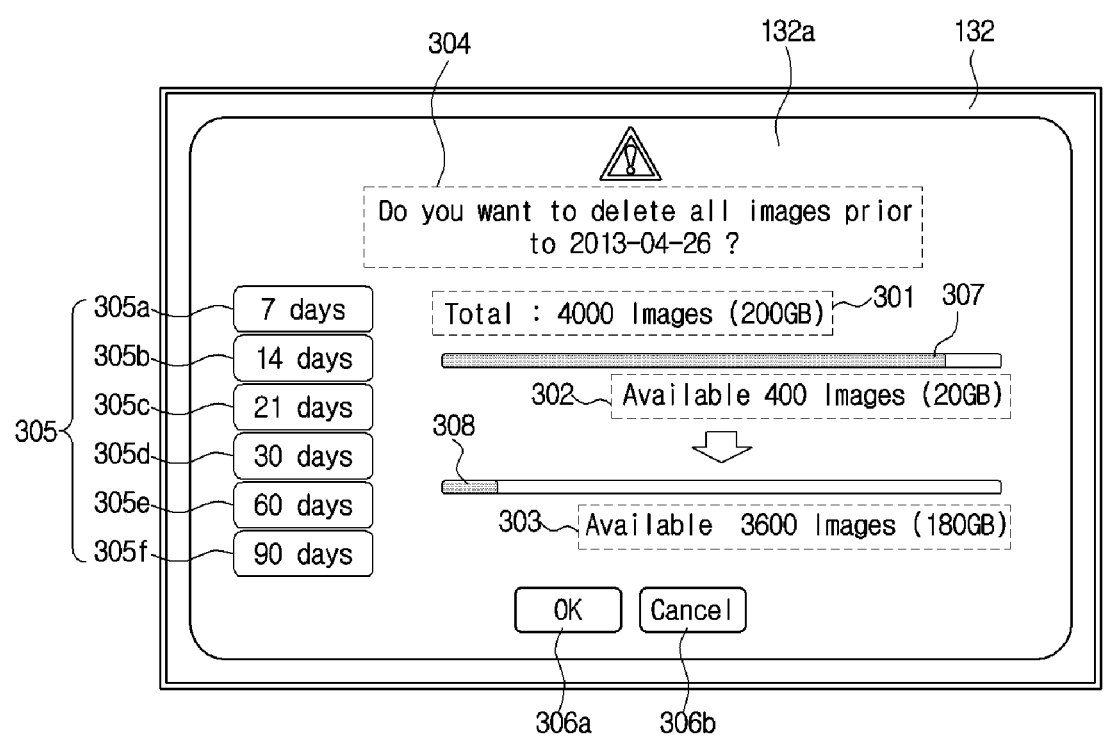
FIG. 6 is a view illustrating an example of a popup window displayed on a display unit.
Figure 7:
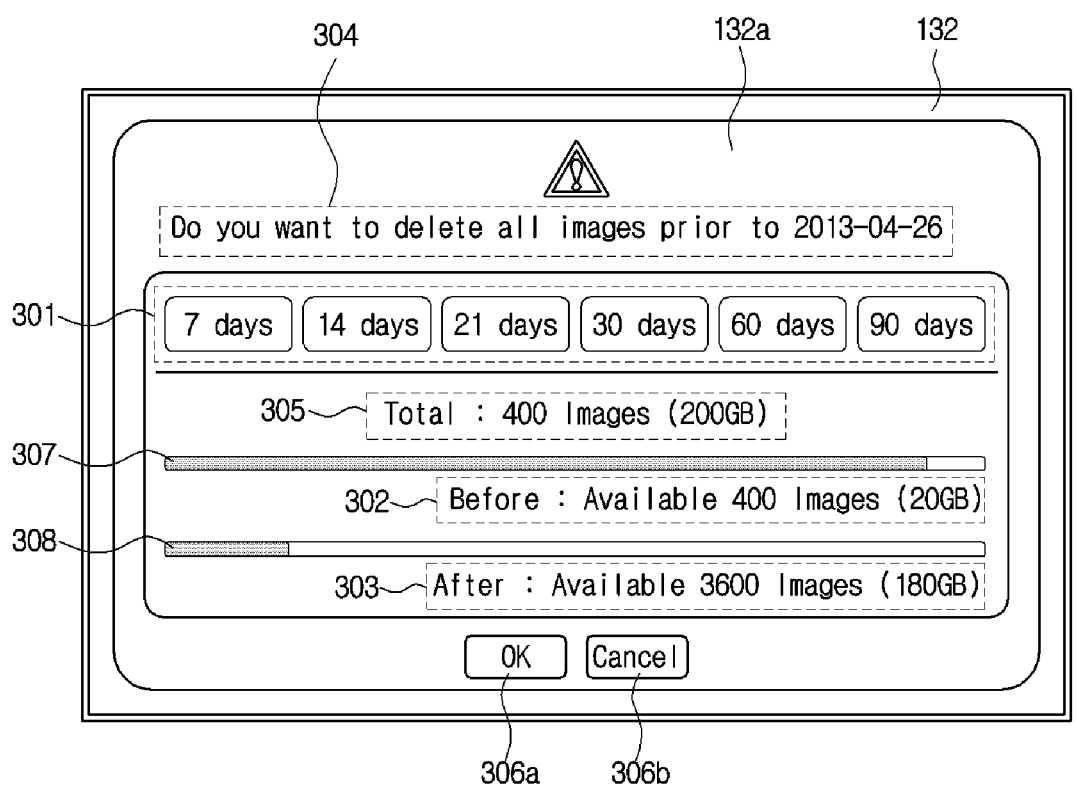
FIG. 7 is a view illustrating an example of the popup window displayed on the display unit.

FIG. 6 is a view illustrating an example of a popup window displayed on the display unit and FIG. 7 is a view illustrating an example of the popup window displayed on the display unit.

Hereinafter, a popup window providing information regarding the storage capacity of the storage unit 140 and guiding input of a command regarding deletion of medical images so that the user may input the command regarding deletion of medical images will be defined as an auto deletion popup window 132a.

With reference to FIG. 6, the auto deletion popup window 132a displays the total storage capacity, the currently used capacity and residual capacity of the storage unit 140, and the used capacity and residual capacity of the storage unit 140 after deletion. The storage capacity may be the maximum number of images which may be stored to allow the user to precisely recognize the storage capacity and may be displayed in a capacity unit (byte) and a bar displaying the storage capacity to assist user intuitive recognition.

In the example of FIG. 6, information regarding the total storage capacity of the storage unit 140 is displayed as text 301 of 4000 images (200 GB). This means that the total storage capacity of the storage unit 140 is 200 GB in which 4000 medical images may be stored. Here, the maximum number of storable medical images indirectly represents the storage capacity, and the numerical value displayed as the data capacity unit directly represents the storage capacity. Further, text 302 representing the current residual capacity is displayed, and text 303 representing the residual capacity after medical image deletion is displayed.

In addition, a guide bar 307 representing the currently used capacity and a guide bar 308 representing the used capacity after medical image deletion may be displayed on a base bar corresponding to the total storage capacity. The horizontal length of the bar may represent the used capacity and additionally, the bar may be colored according to the used capacity.

For example, the bar may be divided into a plurality of levels according to used capacities, and the respective levels may be expressed in different colors. If the used capacity is 0%~60% of the total storage capacity, the bar may be expressed in green (the first level), if the used capacity is 60%~80% of the total storage capacity, the bar may be expressed in yellow (the second level), and if the used capacity is 80%~100% of the total storage capacity, the bar may be expressed in red (the third level). Further, at the same level, as the used capacity increases, brightness or chroma of the color may be changed. Thereby, the user may intuitively recognize the used capacity as compared to the total storage capacity.

The auto deletion popup window 132a displays period setup buttons 305 so that a user may set a reference date for deletion. In more detail, among medical images stored in the storage unit 140, all of medical images prior to a selected reference date for deletion may be deleted. "Medical images prior to the reference date" means medical images acquired prior to the reference date. The reference date for deletion is a date of a specific period (specific days) before a date when deletion is executed. Plural period setup buttons 305 corresponding to different specific periods are provided, and a user may set a reference date for deletion by selecting one of the period setup buttons 305.

In the example of FIG. 6, a period setup button 305a corresponding to 7 days, a period setup buttons 305b corresponding to 14 days, a period setup button 305c corresponding to 21 days, a period setup buttons 305d corresponding to 30 days, a period setup button 305e corresponding to 60 days, and a period setup buttons 305f corresponding to 90 days are displayed.

For example, if a user selects the period setup button 305a corresponding to 7 days, a date 7 days before a date when deletion is executed becomes a reference date for deletion and a confirmation message 304 asking "Do you want to delete all medical images prior to the reference date?" is displayed on the auto deletion popup window 132a.

Selection of one of the period setup buttons 305 may be carried out through the input unit 131. The input unit 131 may be implemented as an input device, such as a mouse, a keyboard, or a track-ball, and the user may select a desired one of the period setup buttons 305 by clicking the one of the period setup buttons 305 displayed on the display unit 132. If the display unit 132 is implemented as a touchscreen, the display unit 132 may perform the function of the input unit 131 and the user may select a desired one of the period setup buttons 305 by touching the one of the period setup buttons 305 displayed on the display unit 132.

The confirmation message 304 of the reference date for deletion and the text 303 and the guide bar 308 representing the storage capacity after deletion are changed according to the reference date for deletion. For this purpose, the image management unit 122 calculates the reference date for deletion according to the selected period setup button 305 and calculates used storage capacity and residual storage capacity after deletion based on the reference date for deletion.

FIG. 6 exemplarily illustrates the case that a user selects the period setup button 305a corresponding to 7 days from among the period setup buttons 305. In this case, on the assumption that the current date when deletion is executed is Aug. 30, 2013, the auto deletion popup window 132a displays the confirmation message 304 asking "Do you want to delete all images prior to 2013 Aug. 23?".

Although the user selects one of the period setup buttons 305, the user may select another of the period setup buttons 305 before selection of a confirm button 306a. Therefore, in FIG. 6, when the user selects the period setup button 305a corresponding to 7 days and then selects another of the period setup buttons 305, the confirmation message 304 of the reference date for deletion, the text 303 representing the residual capacity after deletion, and the guide bar 308 representing the used capacity after deletion are changed to represent information corresponding to the finally selected period setup button 305.

Further, the user may directly set a deleted capacity. In more detail, the user may select the right end of the guide bar 308 representing the used capacity after deletion and drag and drop the right end of the guide art 308 to the left by a distance corresponding to a desired deleted capacity. When drag and drop has been completed, the text 303 representing the storage capacity after deletion may be changed to correspond to the deleted capacity set by drag and drop.

As described above, when setting of the reference date for deletion of medical images has been completed, the user may select the confirm button 306a. When the confirm button 306a is selected, the image management unit 122 deletes all of medical images prior to the reference date set by the user among medical images stored in the storage unit 140. When the medical images are deleted, a DB including various pieces of information of the deleted medical images may be deleted.

If the user does not want to execute medical image deletion, the user may select a cancel button 306b. When the cancel button 306b is selected, the auto deletion popup window 132a displayed on the display unit 132 disappears.

The auto deletion popup window 132a is not limited as to the arrangement of the buttons, the message and the texts displayed on the auto deletion popup window 132a and to the window size of FIG. 6, and may have various arrangements and window sizes as long as the auto deletion popup window 132 may display the above-described contents. Further, the confirmation message 304 is not limited to the text of FIG. 6, and may display various messages as long as they may deliver the above-describe contents.

In the an example of the auto deletion popup window 132a shown in FIG. 7, a confirmation message 304, period setup buttons 305, text 301 representing the total storage capacity, text 302 representing current residual capacity, a guide bar 307 representing currently used capacity, text 303 representing residual capacity after deletion, a guide bar 308 representing used capacity after deletion, and confirm button 306a/cancel button 306b may be arranged in the vertical direction.

Figure 8:
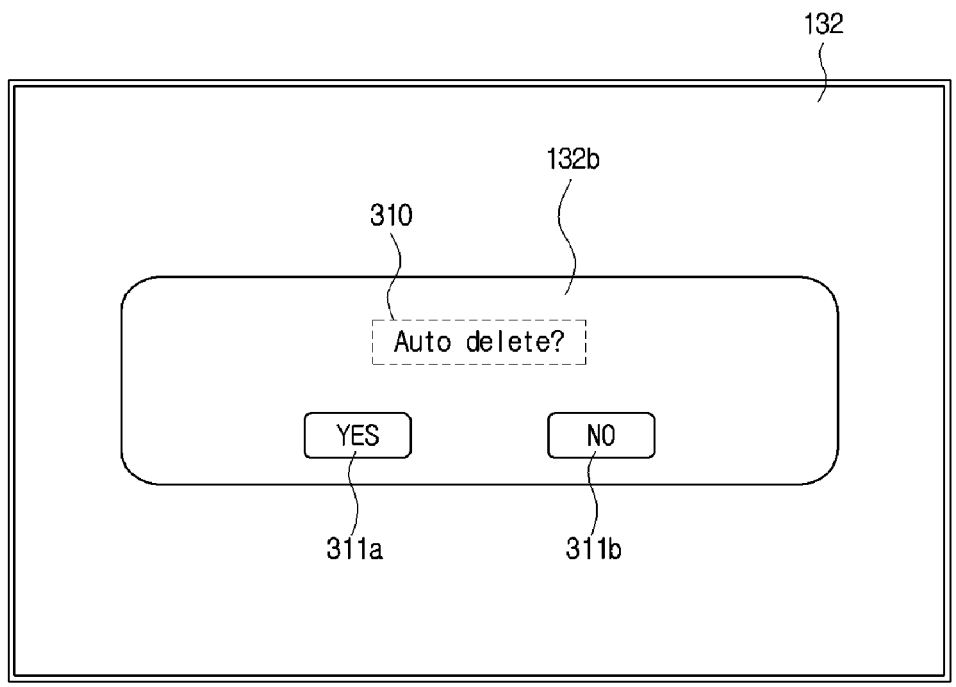
FIG. 8 is a view illustrating an example of a popup window to receive selection as to whether or not auto deletion is executed.
Figure 8:
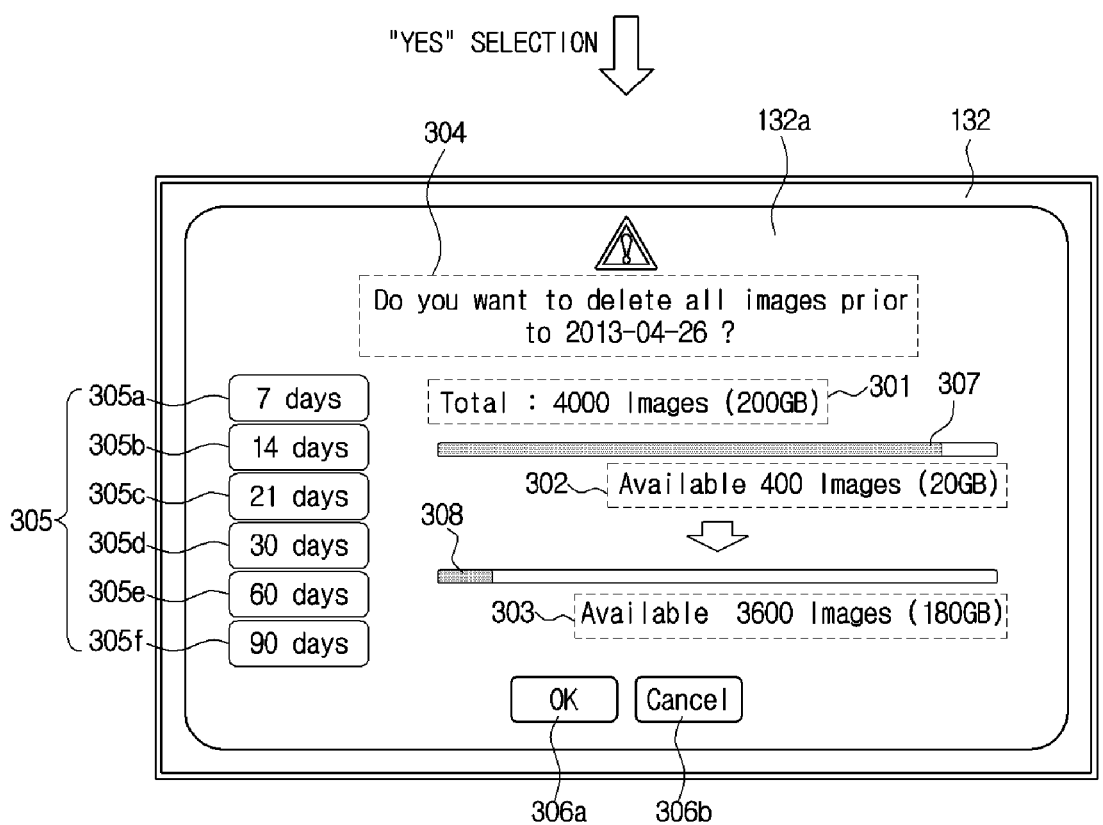

FIG. 8 is a view illustrating an example of a popup window to receive a selection as to whether or not auto deletion is executed.

The display unit 132 may display an information popup window 132b to receive a selection as to whether or not auto deletion is executed from a user prior to display of the auto deletion popup window 132a.

With reference to FIG. 8, an information popup window 132b to receive a selection as to whether or not auto deletion is executed displays a YES button 311a and a NO button 311b allowing the user to select whether or not auto deletion is executed together with a message 310 asking whether or not auto deletion is executed.

When the information popup window 132b is displayed, the user may recognize insufficiency of the current storage capacity of the storage unit 140. When the user selects the YES button 311a, the auto deletion popup window 132a described in FIGS. 6 and 7 is displayed so that information regarding medical image deletion may be provided to the user and the user may select a reference date for deletion. When the user selects the NO button 311b, the information popup window 132b to receive selection as to whether or not auto deletion is executed disappears and auto deletion is not executed.

Figure 9:
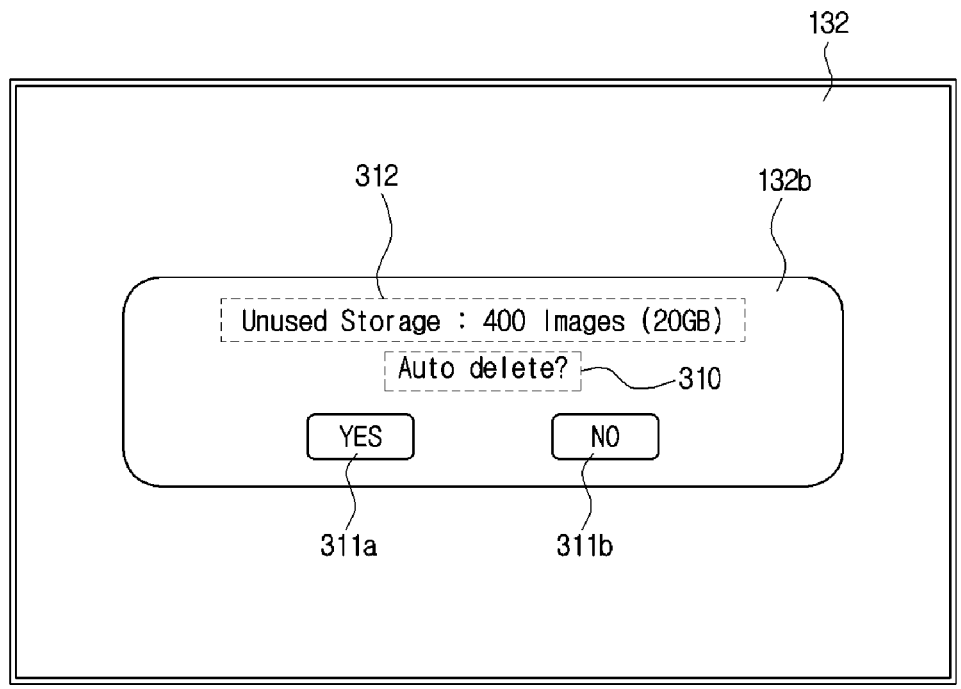
FIG. 9 is a view illustrating an example of the popup window to receive selection as to whether or not auto deletion is executed.
Figure 9:
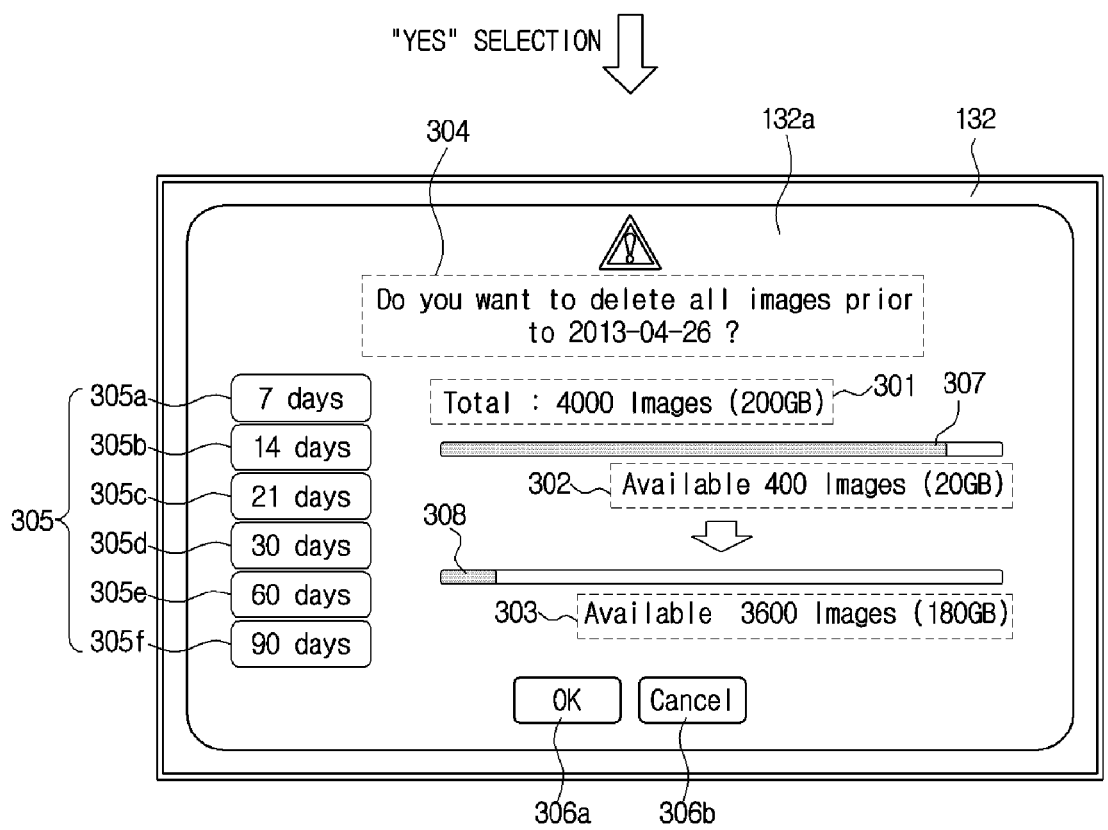

FIG. 9 is a view illustrating an example of the popup window to receive selection as to whether or not auto deletion is executed.

With reference to FIG. 9, the information popup window 132b may display text 312 representing a current residual capacity. In more detail, the text 312 may display the residual capacity calculated by the image management unit 122 and the maximum number of storable medical images at such a residual capacity, thus allowing the user to precisely recognize the current residual capacity and determining whether or not auto deletion is executed.

Instead of numerical display of the current residual capacity, a guide bar 307 representing the currently used capacity may be displayed on a base bar corresponding to the total storage capacity, as exemplarily shown in FIGS. 6 and 7, so that the user may intuitively recognize the current residual capacity.

Figure 10:
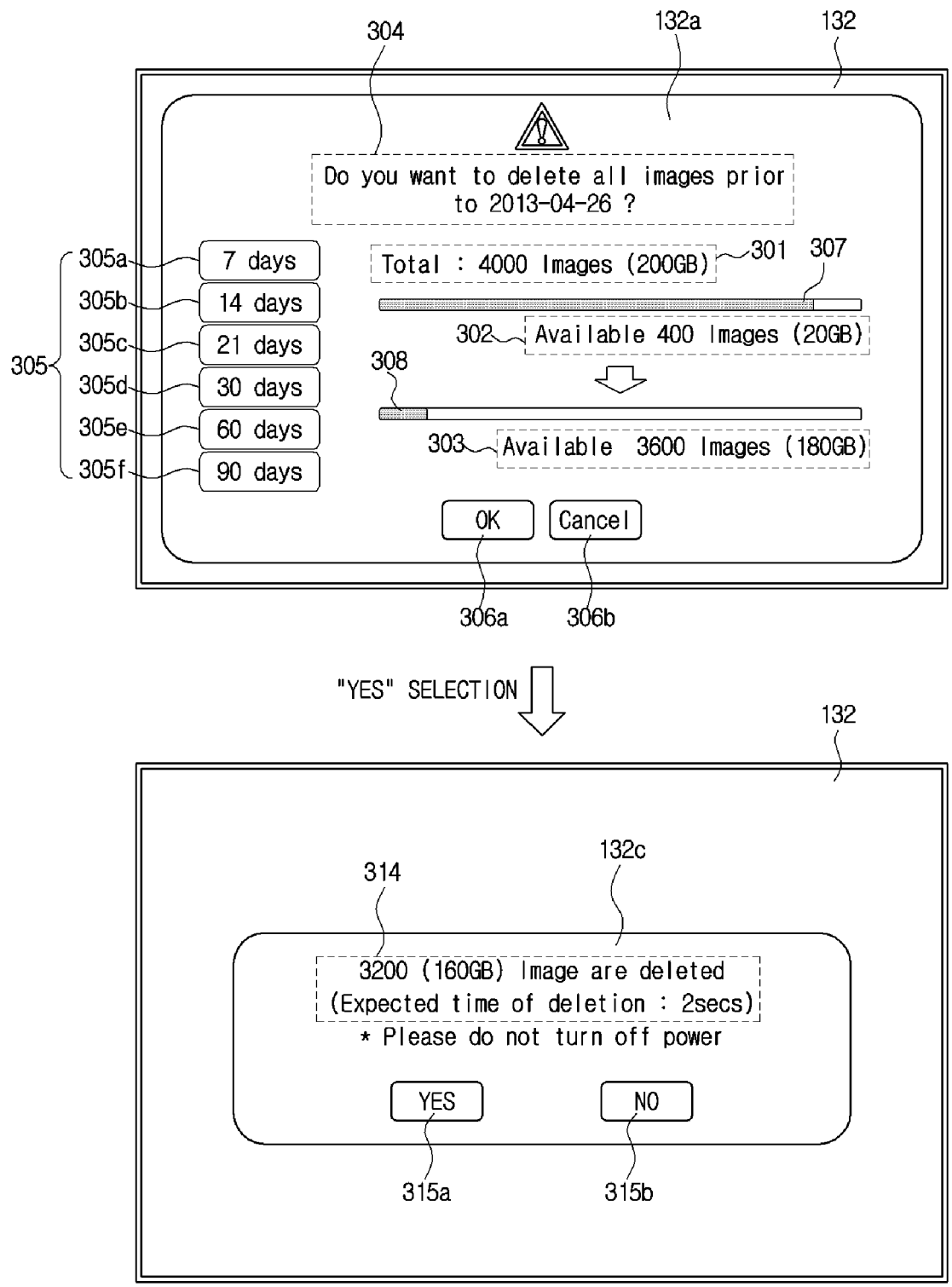
FIG. 10 is a view illustrating a popup window to receive final confirmation regarding medical image auto deletion from a user.

FIG. 10 is a view illustrating a popup window to receive final confirmation regarding medical image auto deletion from a user.

As described above, when the confirm button 306a on the auto deletion popup window 132a is selected, all medical images prior to the set reference date are deleted. The image management unit 122 may cause the display unit 132 to display a final confirmation popup window 132c before medical image deletion is executed.

With reference to FIG. 10, when the confirm button 306a on the auto deletion popup window 132a is selected, the display unit 132 displays the final confirmation popup window 132c. The final confirmation popup window 132c displays a message 314 representing a data capacity to be deleted if auto deletion is executed according to user setting, a confirm button 315a, and a cancel button 315b. The message 314 representing the data capacity to be deleted may display an expected time required for data deletion. The capacity to be deleted may be displayed with the number of deleted medical images and a numerical value having a unit representing the data capacity.

When the user selects the confirm button 315a, the image management unit 122 deletes all medical images prior to the reference date set through the auto deletion popup window 132a and, when the user selects the cancel button 315b, auto deletion is not executed.

Information representing the residual capacity after deletion displayed on the auto deletion popup window 132a may not coincide with information displayed on the final confirmation popup window 132c.

In more detail, when the user selects one of the period setup buttons 305, the text 303 representing the residual capacity and the guide bar 308 are changed nearly in real time. Therefore, the image management unit 122 needs to rapidly calculate deleted capacity corresponding to the selected period setup button 305. Because all medical images do not have the same file size, if actual file sizes of medical images to be deleted are applied, rapid calculation of the deleted capacity may be difficult.

Therefore, the image management unit 122 may calculate the deleted capacity by assuming that the size of one medical image has a predetermined specific value. That is, the deleted capacity calculated by the image management unit 122 may be an estimated value and thus differ from an actual value. For example, on the assumption that a general X-ray image upon which image processing has performed has a size of 48 MB and an original image has a size of 63 MB, the deleted capacity may be calculated by assuming that one medical image has a size of 50 MB. The specific value assumed to be the size of one medical image may be set and changed by the user.

The image management unit 122 calculates a residual capacity after deletion and the maximum number of storable medical images, from the estimated deleted capacity, and displays the calculated residual capacity after deletion and maximum number of medical images on the auto deletion popup window 132a.

However, in a final confirmation stage, i.e., in a stage in which the final confirmation popup window 132c is displayed, a deleted capacity is calculated using actual file sizes of medical images to be deleted and is displayed through the message 314 representing a data capacity to be deleted. Thereby, the user may finally determine whether or not auto deletion is executed based on more precise information.

Figure 11:
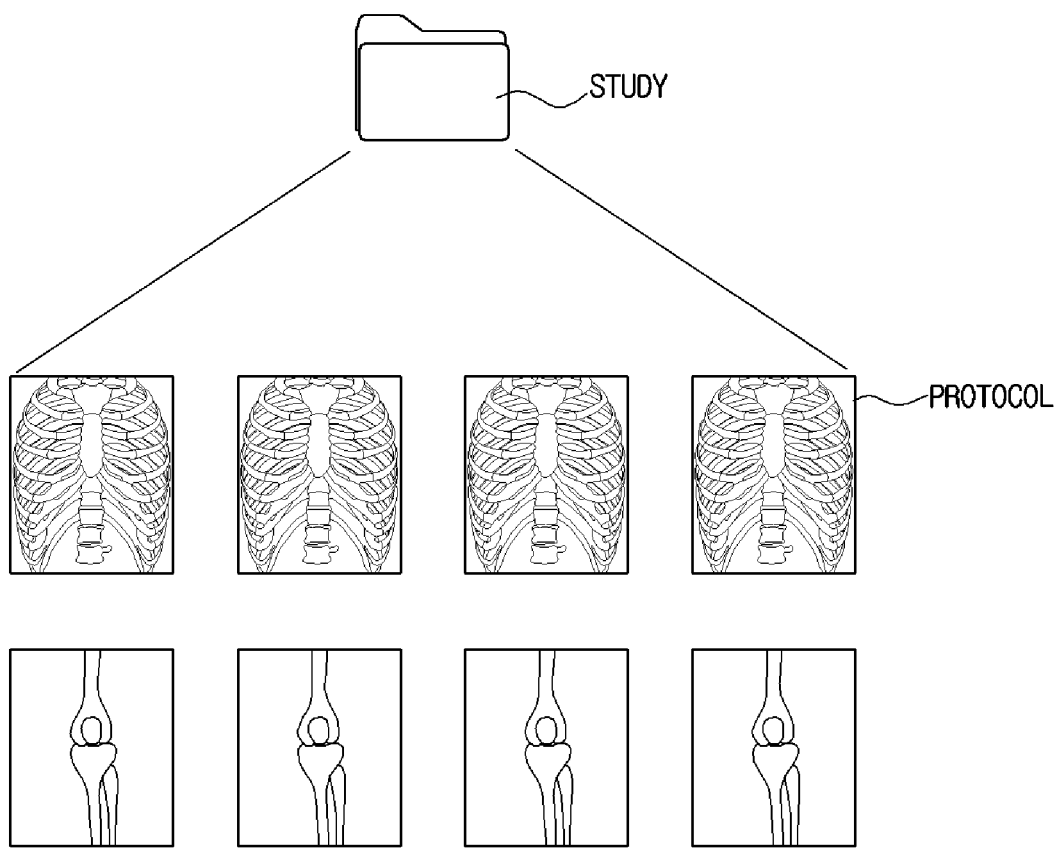
FIG. 11 is a view illustrating a study used as a criterion of image management in the medical imaging apparatus.

FIG. 11 is a view illustrating a study used as a criterion of image management in the medical imaging apparatus.

The image management unit 122 deletes medical images in a study unit, and one study may include one or more medical images.

With reference to FIG. 11, medical images included in a study are referred to as protocols, and protocols included in the same study are stored in one folder. That is, one folder may represent one study.

A criterion for determining which protocols form one study may be determined by user setting. For example, medical images of a traffic accident patient A acquired at a specific date may form one study and, if medical images are acquired in the AM of a specific date and medical images are acquired in the PM of the corresponding specific date, the medical images acquired in the AM may form one study and the medical images acquired in the PM may form another study.

Because medical image deletion is basically carried out in a study unit, the image management unit 122 deletes all studies prior to the reference date for deletion set by the user. Here, if any one of medical images belonging to one study does not correspond to a target to be deleted, such a study is not deleted.

For example, some of medical images belonging to one study may be acquired at a different date from other medical images. This may be the case when medical images are additionally acquired after a designated period from initial imaging or the case that medical images are transferred between studies acquired at different dates. If some of medical images belonging to one study are acquired after the set reference date for deletion, the image management 122 excludes the entirety of the corresponding study from a target to be deleted.

As described above, because, in the stage in which the auto deletion popup window 132a is displayed, rapid calculation by the image management unit 122 is required, calculation of the data capacity to be deleted is not determined in a study unit but may be determined based on acquisition dates of respective medical images. For example, if a medical image is an image acquired prior to the set reference date, although a study to which the medical imaging belongs includes an image acquired after the set reference date, such a medical image may be determined as the target to be deleted.

Further, because, in the stage in which the final confirmation popup window 132c is displayed, the target to be deleted is determined in a study unit, medical images belonging to the same study as an image acquired after the reference date are excluded from the deleted target.

Figure 12:
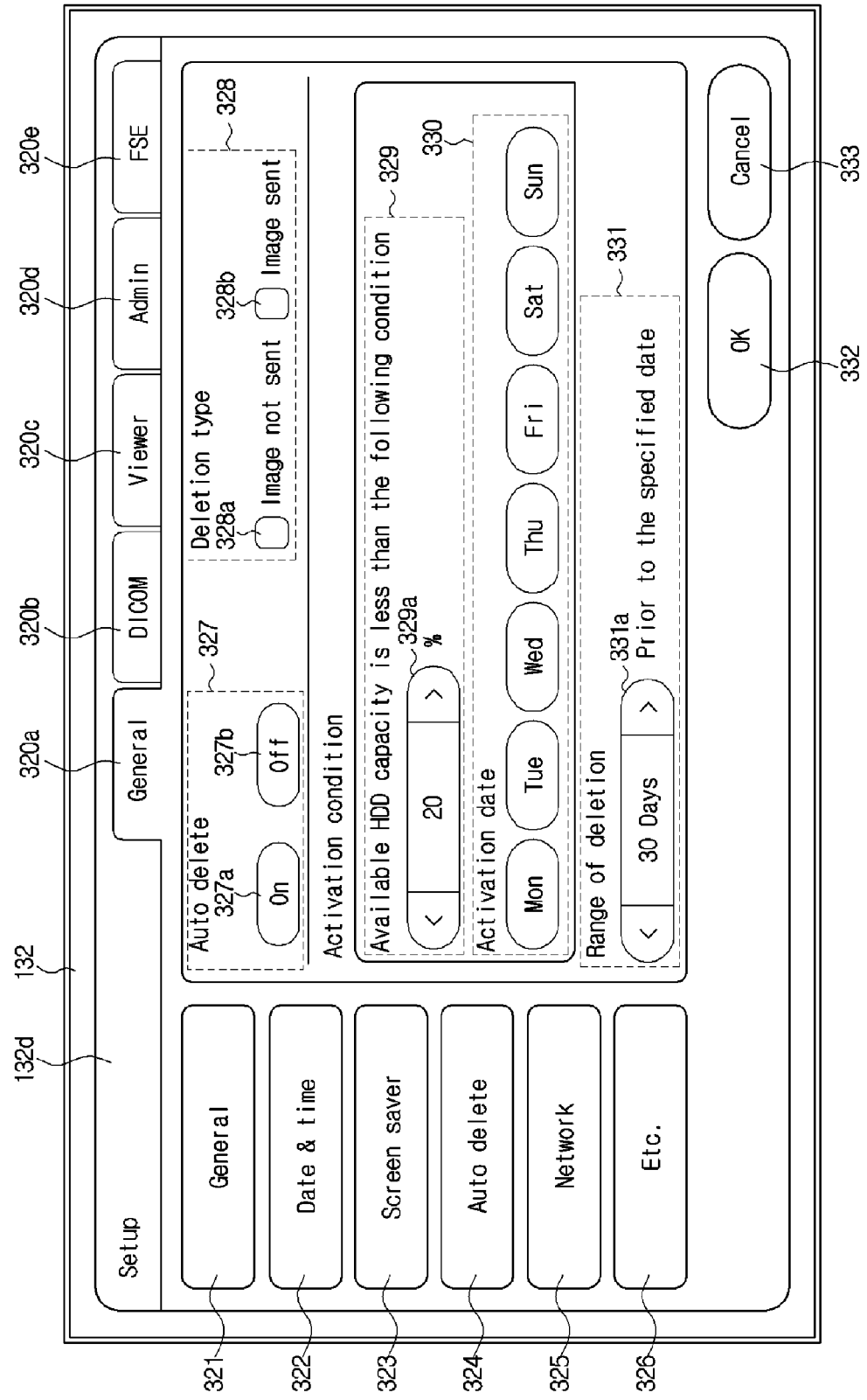
FIG. 12 is a view illustrating an environment setup window to set an environment under which auto deletion may be executed.

FIG. 12 is a view illustrating an environment setup window to set an environment under which auto deletion may be executed.

With reference to FIG. 12, the display unit 132 may display an environment setup window 132d to set the operation environment of the workstation 130. When a general button or tab 320a of the environment setup window 132d is selected, menus which need to be basically set to operate the workstation 130 are displayed in the left region of the environment setup window 132d.

Further, a DICOM menu 320b enables setup regarding DICOM which is a standard protocol to transceive medical images, and a viewer menu 320c enables setup necessary to display images on the display unit 132, for example, which unit is used and which or not the images are aligned at the center, and additionally enables writing of comments regarding a reason for rejection of medical images in the preview stage.

An administrator menu 320d enables setting rights of an administrator, i.e., setting regarding recovery and backup of the DB, setting of a system upgrade cycle, setting of basic values of the imaging parameters, and setting of rights according to users.

Further, an FSE menu 320e may be used by a service engineer, display a log record of the system, and set a language or perform complete initialization of the system.

Hereinafter, the case that the general menu 320a is selected will be described in detail.

The general menu 320a is divided into submenus. When a general submenu 321 is selected, setup regarding booting of the system may be performed and setup regarding reception of the work list may be performed. When a date & time submenu 322 is selected, a format to display date and time may be set. When a screen saver submenu 323 is selected, on/off of a screen saver, a screen saver delay time, and whether or not the system is locked when the screen saver is operated may be set.

Further, when an auto deletion submenu 324 is selected, setup regarding execution conditions of auto deletion may be performed. When a network submenu 325 is selected, setup regarding a LAN card may be performed. When an etc. submenu 326 is selected, remaining environment setup other than the above-described submenu items may be performed.

Hereinafter, the case that the auto deletion submenu 324 is selected will be described in detail. When the auto deletion submenu 324 is selected, a picture regarding execution of auto deletion is displayed on the environment setup window 132d.

In more detail, on/off buttons 327a and 327b may be displayed in an auto delete setup region 327 to turn auto deletion on/off, and type setup buttons 328a and 328b may be displayed in a type setup region 328 to set a type of deleted medical images. The type setup buttons 328a and 328b may be provided as a check box.

Further, a maximum capacity setup button 329a may be displayed in a capacity setup region 329 to set the maximum storage capacity of the storage unit 140 in which auto deletion is executed, and activation date setup buttons may be displayed in a date setup region 330. A period setup button 331a may be displayed in a period setup region 331 to set a base value of a period of deletion. The basic value of the period of deletion may be changed through the auto deletion popup window 132a.

When a store button 332 is selected, the above settings regarding execution of auto deletion are stored and, when a cancel button 333 is selected, the settings stored in advance are maintained.

In order to execute auto deletion, three conditions should be generally satisfied. First, auto deletion should be turned on. Second, the residual capacity of the storage unit 140 should be less than a predetermined value. Third, the current date should correspond to a predetermined activation date.

Auto deletion may be executed only if the above three conditions are satisfied. Therefore, the image management unit 122 may determine whether or not the three conditions are satisfied and execute auto deletion upon determining that the three conditions are satisfied. Here, execution of auto deletion includes a series of processes of displaying the popup windows 132a, 132b, and 132c regarding auto deletion and receiving selection from a user, and medical images are actually deleted if final confirmation for auto deletion is received from the user.

When the system is booted, auto deletion is executed only if three conditions set through the environment setup window 132d are satisfied. However, auto deletion may be executed by calculating the current residual capacity whenever medical imaging is performed.

In more detail, when a medical image is acquired, if the current residual capacity is less than a predetermined reference value, auto deletion may be executed regardless of whether or not auto deletion is turned on or the activation date among the above conditions. Here, the reference value may differ from, i.e., be smaller than, the reference value set through the environment setup window 132d. Further, if the residual capacity is less than the minimum capacity at which additional imaging is enabled, no medical image is acquired.

In the example of FIG. 12, types of medical images to be deleted may be divided into a type of image which is sent and a type of image which is not sent. The type of image which is sent is means an image sent to the PACS, and the type of image which is not sent refers to an image not set to the PACS. A user may select at least one of the two types. If the user selects the type of image sent, images sent to the PACS among medical images acquired prior to the reference date for deletion are deleted and, if the user selects the type of image not sent, images not sent to the PACS among medical images acquired prior to the reference date for deletion are deleted. If the user selects both types, images may be deleted regardless of whether or not the images are sent to the PACS.

Figure 13:
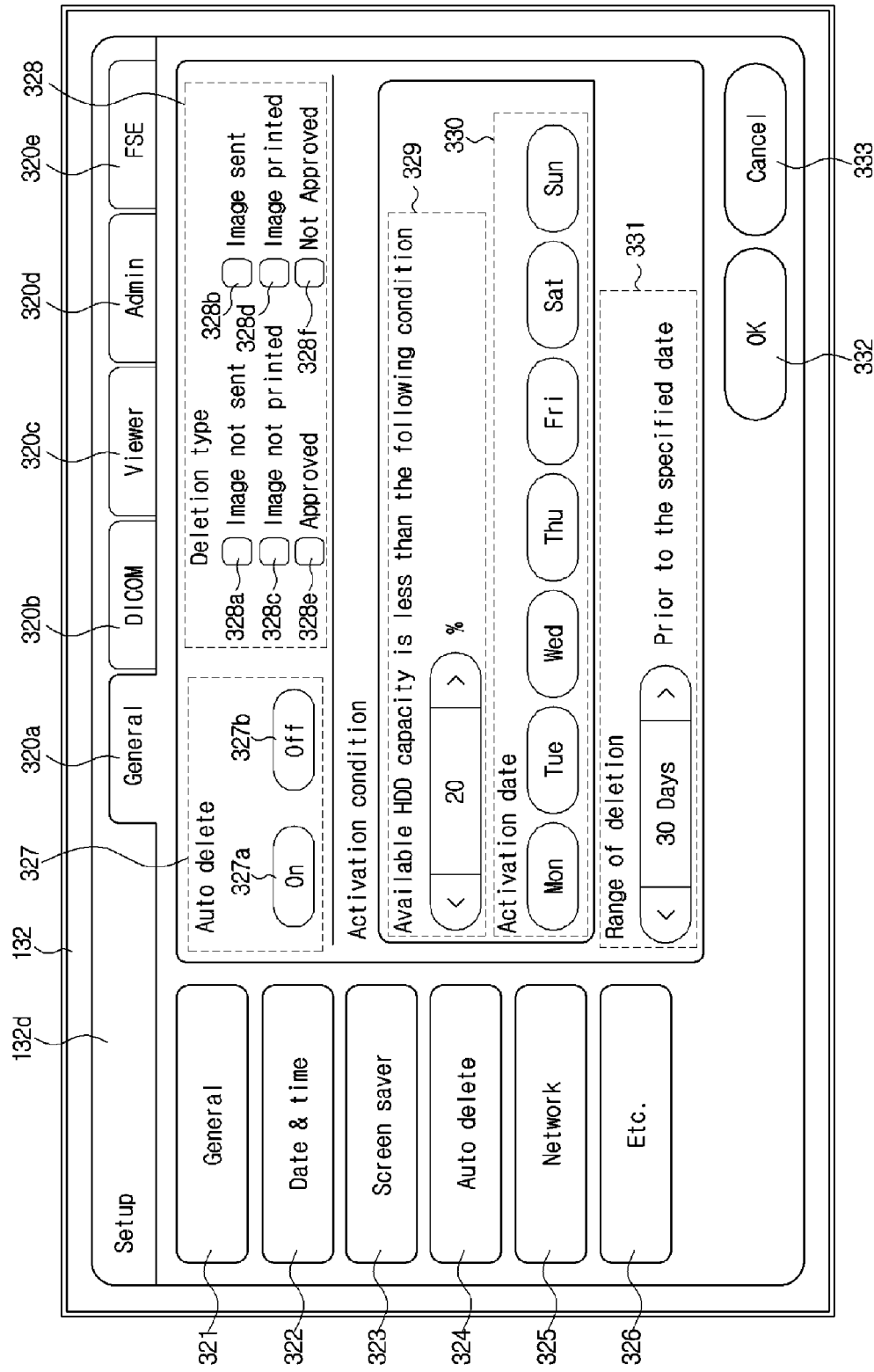
FIG. 13 is a view illustrating an environment setup window displaying further divided kinds of deleted images.

FIG. 13 is a view illustrating an environment setup window displaying further divided kinds of deleted images.

With reference to FIG. 13, types of deleted medical images may be divided not only into a type of image which is sent 328b and a type of image which is not sent 328a, but also into a type of image which is printed 328d, a type of image which is not printed 328c, a type of image which is approved 328e, and a type of image which is not approved 328f.

Although medical images displayed on a screen are generally provided to a user, a hard copy type of medical images printed on printing media may be provided to the user. When the user selects the type of image printed in a type setup region 328, medical images printed on printing media among medical images acquired prior to the reference date for deletion are deleted.

As described above with reference to FIG. 4, when a medical image is acquired, the user may send the medical image to the PACS in the preview stage or the review stage. When the medical image apparatus 100 sends the medical image to the PACS, the PACS sends an approval message, representing that reception of the medical image is normally carried out, to the medical imaging apparatus 100 in response to the reception of the medical image. When the user selects the type of image approved in the type setup region 328, medical images, the approval messages of which have been received from the PACS, among medical images acquired prior to the reference date for deletion may be deleted.

When types of images to be deleted are selected in the type setup region 328, the non-selected type of images may become an exception condition in execution of auto deletion. For example, when the user selects at least one of the type of image sent, the type of image printed, and the type of image approved, at least one of the type of image not sent, the type of image not printed, and the type of image not approved may become an exception condition of auto deletion. Otherwise, according to user selection, at least one of the type of image sent, the type of image printed, and the type of image approved may become an exception condition.

Therefore, when auto deletion is executed, the image management unit 122 may determine whether or not there is an exception condition. The data capacity to be deleted may be calculated in consideration of the exception condition in the display stage of the auto deletion popup window 132, or the exception condition is not considered in the display stage of the auto deletion popup window 132a to rapidly display the auto deletion popup window 132a and may be considered in the display stage of the final confirmation popup window 132c.

Figure 14:
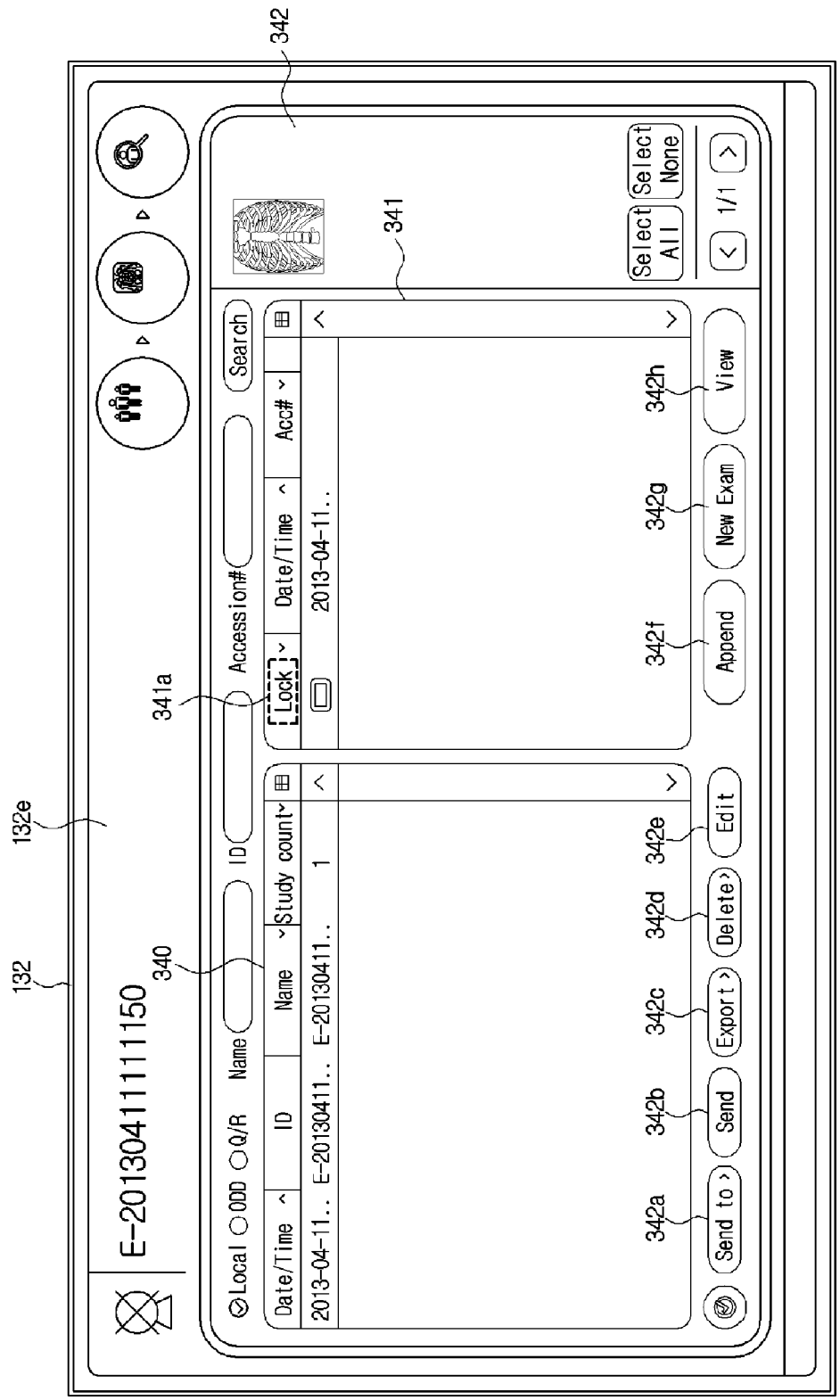
FIG. 14 is a view illustrating a review window to set a lock according to studies.

FIG. 14 is a view illustrating a review window to set a lock according to studies.

In addition to the above-described exception condition, the user may set a lock of a separate study desired to be excluded from auto deletion. For this purpose, when the display unit 132 displays a lock setup picture, the user may set a lock of a desired study on the lock setup picture.

For example, setting of a lock according to studies may be carried out through a review window 132e. The review picture 132e is displayed on the display unit 132 in the review stage described with reference to FIG. 4, and may perform various functions in addition to a lock setting function. First, the lock setting function will be described.

With reference to FIG. 14, the review window 132e includes a study list region 340 and a protocol list region 341. Studies stored in the storage unit 140 are listed in the study list region 340 and, when one of the listed studies is selected, information of protocols (medical images) included in the selected study may be displayed in the protocol list region 341. Further, an image display region 342 displaying images of the protocols included in the selected study may be provided in another region of the review window 132e.

A toggle type lock button 341a may be displayed in the protocol list region 341. When the lock button 341a is selected, a lock of the corresponding study is set and all protocols included in the corresponding study are excluded from auto deletion even if the protocols are acquired prior to the reference date for deletion. Further, manual deletion or editing of the study, a lock of which is set, by the user may be disabled.

Therefore, when auto deletion is executed, the image management unit 122 determines whether or not there is any study, a lock of which is set, among studies acquired prior to the reference date for deletion and excludes a study (studies), a lock of which is set, from auto deletion. The data capacity to be deleted may be calculated in consideration of whether or not there is any study, a lock of which is set, in the display stage of the auto deletion popup window 132a, or whether or not there is any study, a lock of which is set, is not considered in the display stage of the auto deletion popup window 132a to rapidly display the auto deletion popup window 132a and may be considered in the display stage of the final confirmation popup window 132c.

The user may perform review, such as editing and sending of medical images through the review window shown in FIG. 14. In more detail, the review window 132e may display a target button 342a, a send button 342b, an export button 342c, a delete button 342d, an edit button 342e, an append button 342f, a new examination button 342g, and a view button 342h.

When at least one of studies listed in the study list region 340 is selected, operations of the selected study, such as sending, export, deletion, editing, appending, and view, may be performed. Such operations may be performed upon the entirety of the study or performed upon some or individual protocols displayed in the protocol list region 341.

When the target button 342a is selected, a list of plural PACS in the hospital may be displayed and the user may select a PACS to which medical images are sent. When the send button 342b is selected, the image management unit 122 sends selected medical images to the selected PACS.

When the export button 342c is selected, the selected medical images are exported to an external storage medium, such as a CD or a DVD. In this case, medical images which are not exported to the external storage medium may be set as an exception condition excluded from auto deletion. Although the export button 342c is selected, the medical images are not immediately exported and a window to performing setting regarding export may be first displayed. This will be described later.

When the delete button 342d is selected, the selected study or selected protocols may be deleted. When the edit button 342e is selected, editing of the selected medical images may be performed. For example, the selected medical images may be amended, moved to other studies, or copied and swapped with medical images of other studies.

When the append button 342f is selected, additional imaging of the selected study is performed. When the new examination button 342g is selected, imaging of a new study is performed. When the view button 342h is selected, editing tools are displayed together with a medical image.

Figure 15:
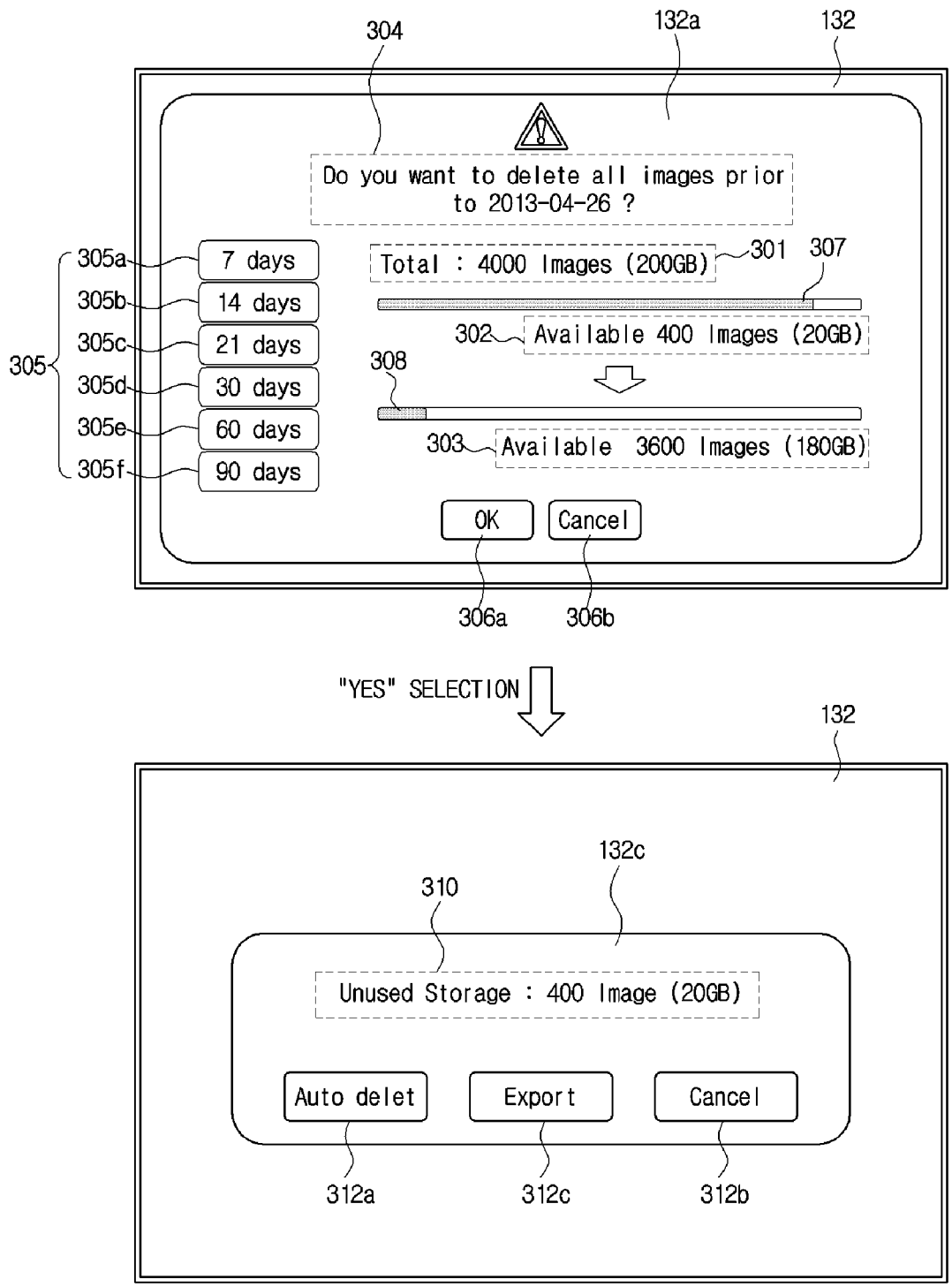
FIG. 15 is a view illustrating an example of the information popup window displayed on the display unit.
Figure 16:
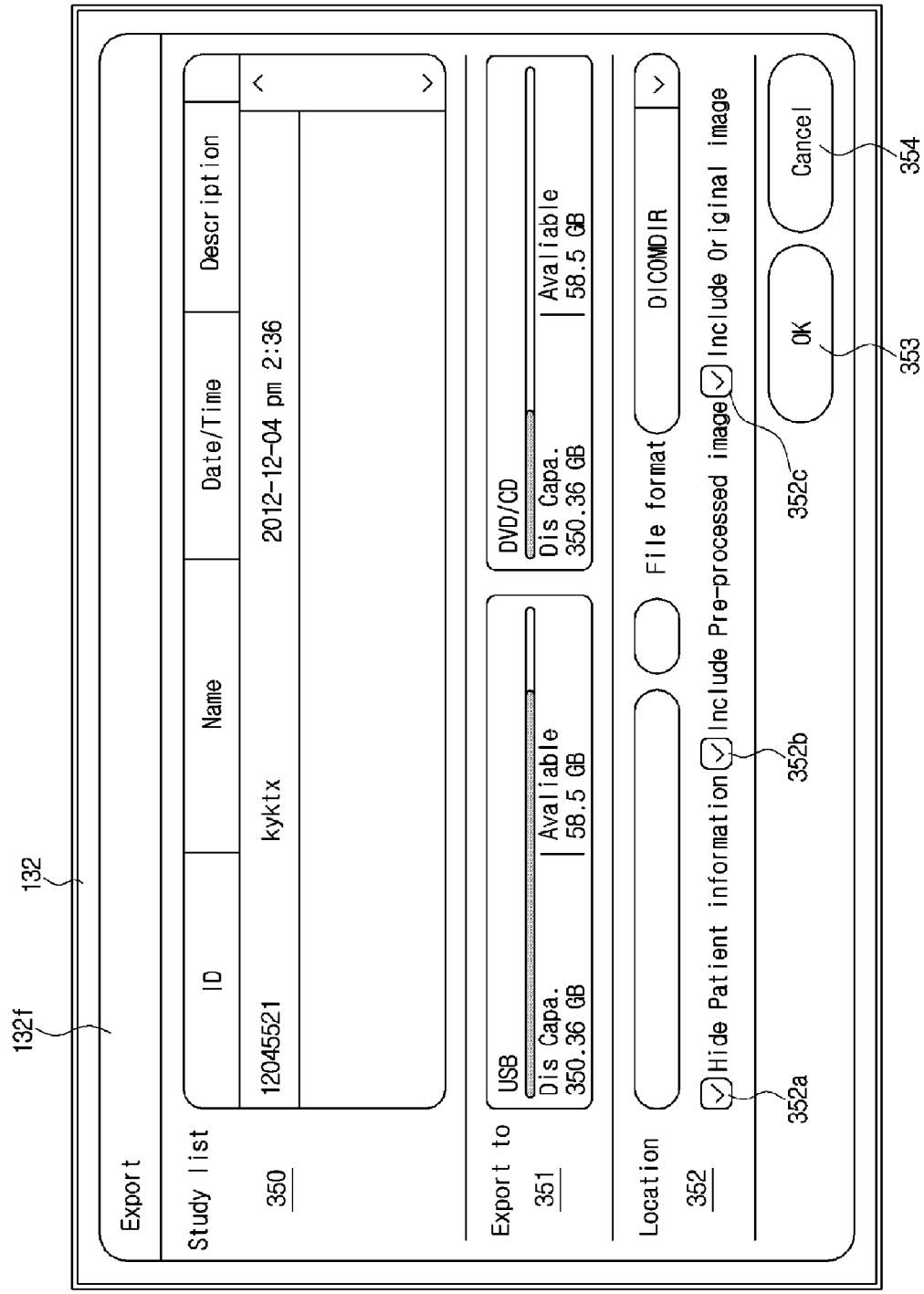
FIG. 16 is a view illustrating an export setup window.

FIG. 15 is a view illustrating an example of the information popup window displayed on the display unit and FIG. 16 is a view illustrating an export setup window.

In the above-described embodiment, when the residual capacity is less than the set reference value, the information popup window 132b is displayed to receive selection regarding execution or cancel of auto deletion from a user. However, instead of auto deletion, an export of medical images may be executed according to user selection.

For this purpose, the information popup window 132c displayed on the display unit 132, as exemplarily shown in FIG. 15, further includes an export button 312c in addition to a button 312a to select auto deletion and a cancel button 312b. When the export button 312c is selected, an export setup window 132f to perform setting regarding export may be displayed, as exemplarily shown in FIG. 16.

The entirety of a study list stored in the storage unit 140 or a study list within the period of deletion set through the environment setup window 132d may be displayed in a study list region 350 of the export setup window 132f, and IDs, names, acquisition dates and descriptions may be displayed in the study list to assist the user to determine studies to be exported to the external storage medium.

Further, types of external storage media to which studies may be exported and information regarding the storage capacities thereof may be displayed in an external storage medium information region 351, and the user may select an external storage medium to which studies will be exported.

A select button 352a regarding the hiding of patient information, a select button 352b regarding export of the preview images, and a select button 352c regarding export of the original images may be displayed in an information selection region 352 of the export setup window 132f. The select buttons 352a, 352b, and 352c may be provided as a check box. The user may pick out information which should not be exported to the external storage medium by selecting a proper one of the select buttons 352a, 352b, and 352c.

When a confirm button 353 is selected, the image management unit 122 exports the medical images to the external storage medium and, when a cancel button 354 is selected, operation for export setting is ended.

In order to protect patient information, user rights of the data export function may be granted to a specific user alone. In this case, when the user selects the export button 312c on the final confirmation popup window 132c, an authentication popup window to authenticate user rights may be displayed so that the export setup window 132f may be displayed only to an authenticated user.

Otherwise, when the user selects the export button 312c, the image management unit 122 may directly authenticate rights of the user based on log-in information of the user and display the export setup window 132f to an authenticated user only.

Further, if the export button 342 on the review window 132e shown in FIG. 14 is selected, the above-described authentication of user rights may be performed.

Hereinafter, a medical image management method in accordance with an embodiment of the present disclosure will be described. Such a medical image management method may be performed using the above-described medical imaging apparatus 100.

Figure 17:
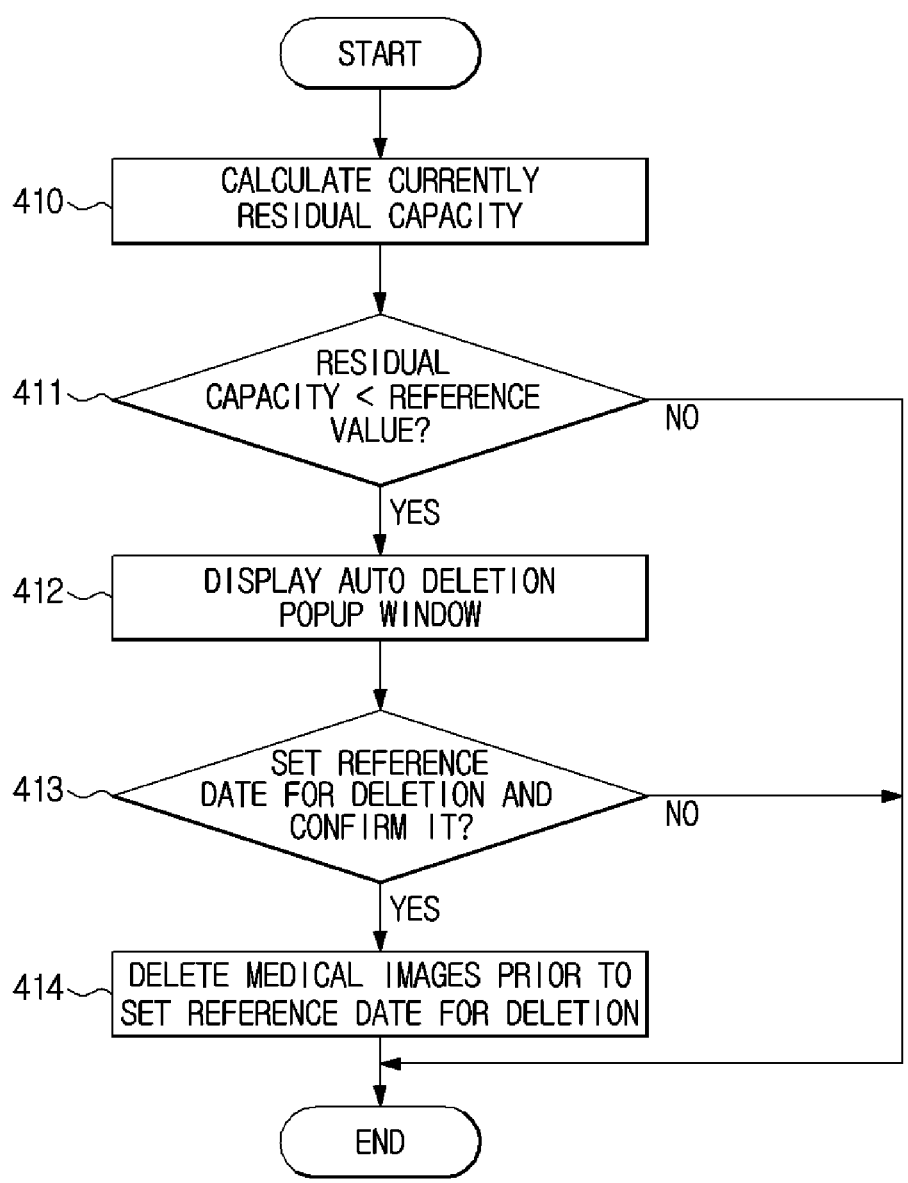
FIG. 17 is a flowchart illustrating a medical image management method in accordance with an embodiment of the present disclosure.

FIG. 17 is a flowchart illustrating a medical image management method in accordance with an embodiment of the present disclosure.

With reference to FIG. 17, a current residual capacity is calculated (Operation 410) and, if the calculated residual capacity is less than a predetermined reference value (Yes in Operation 411), an auto deletion popup window is displayed (Operation 412). The reference value compared to the residual capacity may be set and changed by a user.

Operation 410 to Operation 412 may be performed upon booting the medical imaging apparatus 100 or logging in to the workstation 130, be performed whenever a medical image is acquired, or be performed at a designated cycle. If Operation 410 to Operation 412 may be performed whenever a medical image is acquired, the reference value compared to the residual capacity may be set to be smaller and, if the residual capacity is less than the minimum capacity at which imaging is enabled, no medical image may be acquired.

As exemplarily shown in FIG. 12, execution conditions of auto deletion may be set through the environment setup window 132d. Whether or not auto deletion is turned on, whether or not the current date corresponds to an auto deletion activation date may be determined together with calculation of the current residual capacity and comparison between the calculated current residual capacity and the reference value (Operations 410 and 411), the auto deletion popup window may be displayed if the three conditions (turning-on of auto deletion, the auto deletion activation date, and the residual capacity of less than the reference value) are satisfied.

The user may set a period of deletion of medical images by selecting one of the period setup buttons 305, and set a reference date for deletion using the set period of deletion. For example, when the period setup button 305 corresponding to 7 days, a date 7 days before the current date is set as the reference date for deletion.

The confirmation message 304 regarding the reference date for deletion, the text 303 representing the residual capacity after deletion, and the guide bar 308 representing the used capacity after deletion on the auto deletion popup window 132a are changed according to the reference date for deletion. For this purpose, the reference date for deletion is calculated according to selection of the period setup button 305, and the used capacity and residual capacity after deletion are calculated based on the reference date for deletion. A description of the guide bar 308 representing the used capacity after deletion has been given above with reference to FIG. 6.

When setting of the reference date for deletion and user confirmation have been completed (Yes in Operation 413), medical images prior to the set reference date for deletion are deleted (Operation 414). Deletion of medical images may be carried out in a study unit. Therefore, if any one of medical images belonging to one study is not acquired prior to the reference date for deletion, the entirety of the study may be excluded from deletion.

Figure 18:
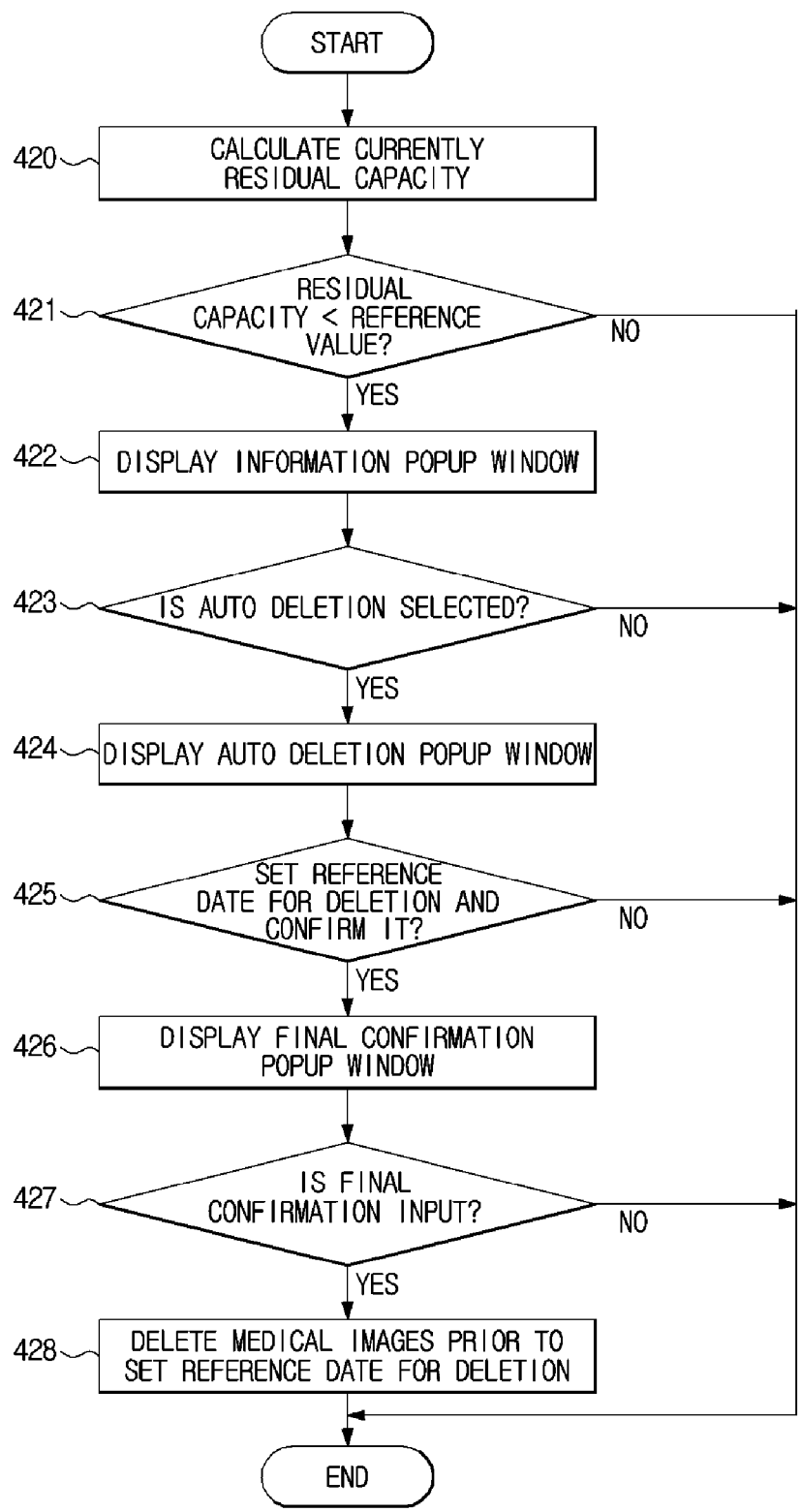
FIG. 18 is a flowchart illustrating a method of displaying popup windows by stages, in the medical image management method in accordance with an embodiment of the present disclosure.

FIG. 18 is a flowchart illustrating a method of displaying popup windows by stages, in the medical image management method in accordance with the embodiment of the present disclosure.

With reference to FIG. 18, a current residual capacity is calculated (Operation 420), and whether or not the calculated current residual capacity is less than a predetermined reference value is determined (Operation 421). A description of Operations 420 and 421 is the same as the description of Operations 410 and 411 of FIG. 17.

If the residual capacity is less than the predetermined reference value (Yes in Operation 421), the information popup window 132b is displayed (Operation 422). The information popup window 132b receives confirmation, as to whether or not auto deletion is executed before display of the auto deletion popup window 132*a*, from a user. The information popup window 132*b* may display information regarding the current residual capacity.

When auto deletion is selected (Yes in Operation 423), the auto deletion popup window 132*a* is displayed (Operation 424). Thereafter, the user may set a period of deletion of medical images by selecting one of the period setup buttons 305 on the auto deletion popup window 132*a*, and a reference date for deletion may be set by the set period of deletion.

When setting of the reference date for deletion and user confirmation have been completed (Yes in Operation 425), the final confirmation popup window 132*c* is displayed (Operation 426). The final confirmation popup window 132*c* may display a data capacity which will be actually deleted with the maximum number of storable medical images and a numerical value of a data capacity unit, and the user may confirm the data capacity which will be actually deleted and perform final confirmation or cancel deletion.

When final confirmation is input by the user (Yes in Operation 427), medical images prior to the reference date for deletion are deleted (Operation 428).

Figure 19:
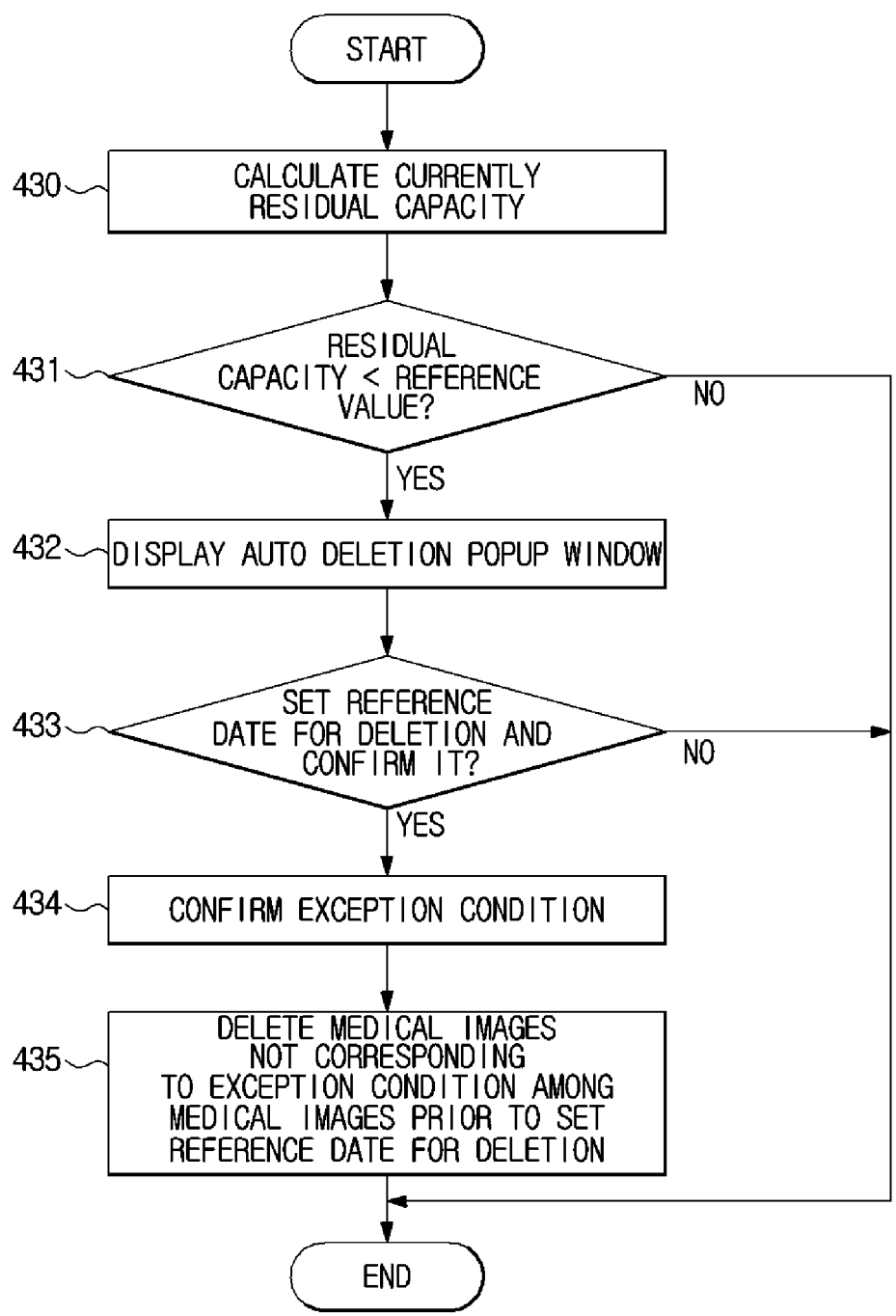
FIG. 19 is a flowchart illustrating a method of confirming an exception condition, in the medical image management method in accordance with an embodiment of the present disclosure.

FIG. 19 is a flowchart illustrating a method of confirming an exception condition, in the medical image management method in accordance with the embodiment of the present disclosure.

With reference to FIG. 19, a current residual capacity is calculated (Operation 430), and if the calculated residual capacity is less than a predetermined reference value (Yes in Operation 431), the auto deletion popup window 132*a* is displayed (Operation 432). A description of Operations 430 to 432 is the same as the description of FIG. 17.

A user may set a period of deletion of medical images by selecting one of the period setup buttons 305 on the auto deletion popup window 132*a*, and a reference date for deletion may be set by the set period of deletion.

When setting of the reference date for deletion and user confirmation have been completed (Yes in Operation 433), an exception condition is confirmed (Operation 434). The exception condition may be set by the user or the system, and include whether or not medical images are sent to the PACS, whether or not medical images are printed on printing media into a hard copy type, or whether or not sending approval messages from the PACS are received. Further, the exception condition may include whether or not a lock of any study is set.

Among the medical images prior to the set reference date for deletion, medical images which do not correspond to the exception condition are deleted (Operation 435). Because deletion of medical images may be carried out in a study unit, if any one of medical images belonging to one study is not acquired prior to the reference date for deletion or corresponds to the exception condition, the entirety of the study may be excluded from deletion.

Figure 20:
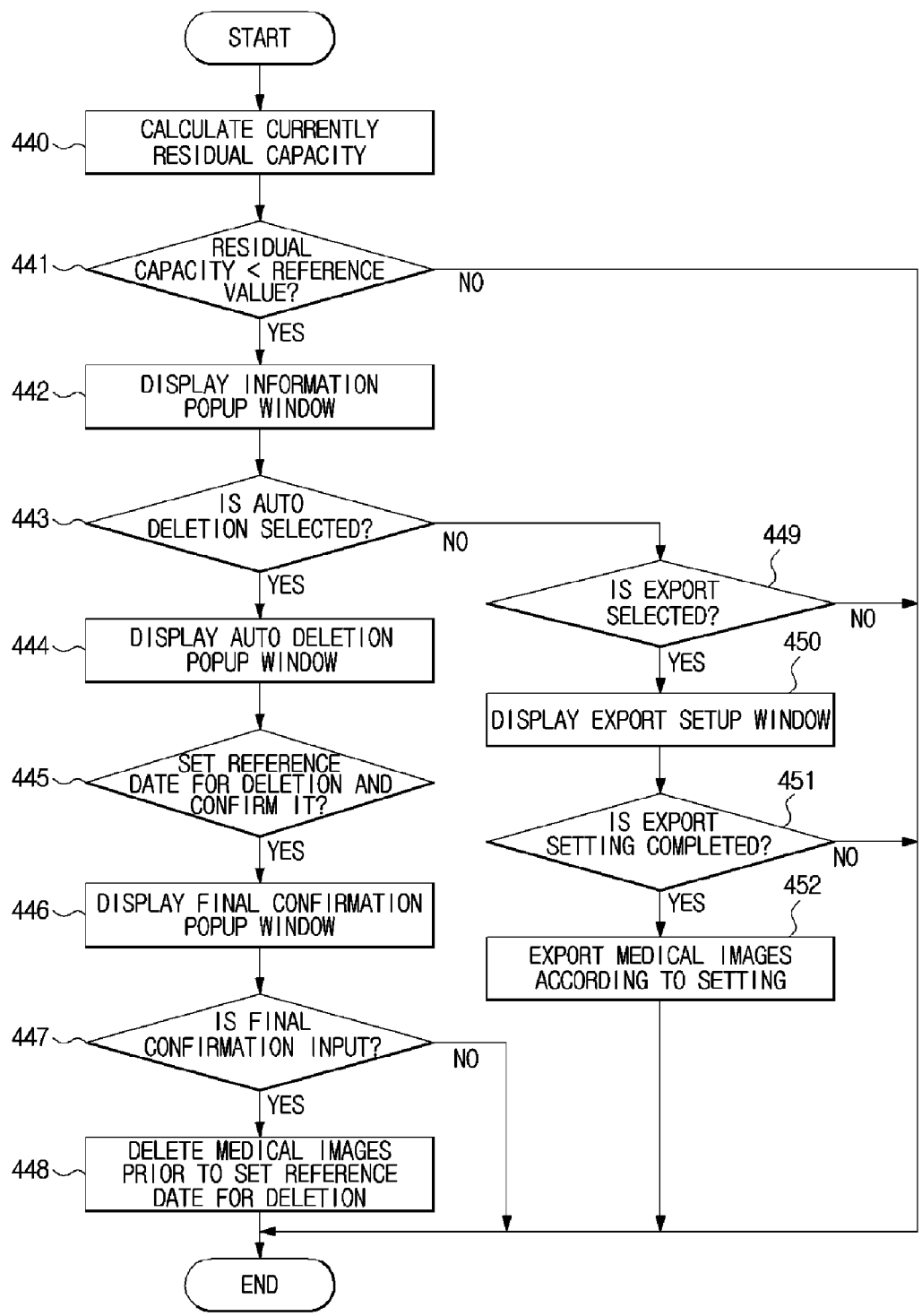
FIG. 20 is a flowchart illustrating a method of performing image export, in the medical image management method in accordance with an embodiment of the present disclosure.

FIG. 20 is a flowchart illustrating a method of performing image export, in the medical image management method in accordance with the embodiment of the present disclosure.

With reference to FIG. 20, a current residual capacity is calculated (Operation 440), and whether or not the calculated current residual capacity is less than a predetermined reference value is determined (Operation 441).

If the residual capacity is determined to be less than the predetermined reference value (Yes in Operation 441), the information popup window 132*b* is displayed (Operation 442). The information popup window 132*b* receives confirmation, as to whether or not auto deletion is executed before display of the auto deletion popup window 132*a*, from a user.

When auto deletion is selected (Yes in Operation 443), the auto deletion popup window 132*a* is displayed (Operation 444). Thereafter, the user may set a period of deletion of medical images by selecting one of the period setup buttons 305 on the auto deletion popup window 132*a*, and a reference date for deletion may be set by the set period of deletion.

When setting of the reference date for deletion and user confirmation have been completed (Yes in Operation 445), the final confirmation popup window 132*c* is displayed (Operation 446). The final confirmation popup window 132*c* may display a data capacity which will be actually deleted with the maximum number of storable medical images and a numerical value of a data capacity unit, and the user may confirm the data capacity which will be actually deleted and perform final confirmation or cancel deletion.

When final confirmation is input by the user (Yes in Operation 447), medical images prior to the reference date for deletion are deleted (Operation 448). At this time, medical images, which do not correspond to an exception condition, may be deleted by performing confirmation of the exception condition.

When image export is selected (Yes in Operation 449), the export setup window 132*f* is displayed (Operation 450). When export setting through the export setup window 132*f* has been completed (Yes in Operation 451), the medical images are exported to an external storage medium according to the setting (Operation 452).

In order to protect patient information, user rights of the data export function may be granted to a specific user alone. In this case, when the user selects the export button 312*c* on the final confirmation popup window 132*c*, the authentication popup window to authenticate user rights may be displayed so that the export setup window 132*f* may be displayed only to an authenticated user.

Otherwise, when the user selects the export button 312*c*, rights of the user may be directly authenticated based on log-in information of the user and the export setup window 132*f* may be displayed only to an authenticated user.

In the above-described medical imaging apparatus and medical image management method, if the residual capacity of the storage unit is insufficient, the auto deletion popup window is displayed so that a user may select a period of deletion, and information regarding the current capacity and the capacity after deletion may be displayed with numerical values and figures on the auto deletion popup window, thus allowing the user to simultaneously acquire precise information and intuitive information.

Therefore, deletion of medical images unintended by the user may be prevented, and the capacity of the storage unit in which medical images are stored may be effectively managed and thus a difficulty in imaging due to insufficient capacity of the storage unit may be prevented.

As is apparent from the above description, in a medical imaging apparatus and a medical image management method in accordance with an embodiment of the present disclosure, information regarding medical image deletion is provided to a user upon deleting stored medical images, thus allowing the user to intuitively recognize a storage capacity and to select a data capacity to be deleted.

The above-described embodiments may be recorded in computer-readable media including program instructions to implement various operations embodied by a computer. The media may also include, alone or in combination with the program instructions, data files, data structures, and the like. The program instructions recorded on the media may be those specially designed and constructed for the purposes of embodiments, or they may be of the kind well-known and available to those having skill in the computer software arts. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The computer-readable media may also be a distributed network, so that the program instructions are stored and executed in a distributed fashion. The program instructions may be executed by one or more processors. The computer-readable media may also be embodied in at least one application specific integrated circuit (ASIC) or Field Programmable Gate Array (FPGA), which executes (processes like a processor) program instructions. Examples of program instructions include both machine code, such as produced by a compiler, and files containing higher level code that may be executed by the computer using an interpreter. The above-described devices may be configured to act as one or more software modules in order to perform the operations of the above-described embodiments, or vice versa.

Although a few embodiments of the present disclosure have been shown and described, it would be appreciated by those skilled in the art that changes may be made in these embodiments without departing from the principles and spirit of the invention, the scope of which is defined in the claims and their equivalents.

What is claimed is:

1. A medical imaging apparatus comprising:
a storage unit storing medical images;
a controller calculating a residual capacity of the storage capacity of the storage unit and determining whether the calculated residual capacity is less than a predetermined reference value; and
a display unit displaying an auto deletion popup window receiving setup information regarding a reference date for deletion of the stored medical images, if determined that the calculated residual capacity is less than the predetermined reference value.

2. The medical imaging apparatus according to claim 1, wherein the auto deletion popup window includes a plurality of period setup buttons corresponding to periods determining the reference date for deletion.

3. The medical imaging apparatus according to claim 2, wherein:
the controller, if one of the plurality of period setup buttons is selected, determines the reference date for deletion based on the selected period setup button; and
the display unit displays the determined reference date for deletion on the auto deletion popup window.

4. The medical imaging apparatus according to claim 1, wherein the display unit displays information regarding the total storage capacity and current residual capacity of the storage unit on the auto deletion popup window.

5. The medical imaging apparatus according to claim 4, wherein the information regarding the total storage capacity and current residual capacity of the storage unit includes the maximum number of storable medical images or a numerical value displayed as a unit representing a storage capacity.

6. The medical imaging apparatus according to claim 1, wherein the display unit displays information regarding the currently used capacity of the storage unit on the auto deletion popup window.

7. The medical imaging apparatus according to claim 6, wherein the information regarding the currently used capacity of the storage unit is displayed as a guide bar having a length proportional to the currently used capacity.

8. The medical imaging apparatus according to claim 7, wherein the display unit displays the guide bar in different colors according to currently used capacities.

9. The medical imaging apparatus according to claim 6, wherein the controller calculates a used capacity and a residual capacity after deletion of medical images being a target to be deleted among the medical images stored in the storage unit, if the reference date for deletion is set.

10. The medical imaging apparatus according to claim 9, wherein the display unit displays information regarding the used capacity and residual capacity after deletion on the auto deletion popup window.

11. The medical imaging apparatus according to claim 10, wherein the information regarding the used capacity after deletion is displayed as a guide bar having a length proportional to the used capacity after deletion.

12. The medical imaging apparatus according to claim 11, wherein the display unit displays the guide bar in different colors according to used capacities after deletion.

13. The medical imaging apparatus according to claim 9, wherein the controller deletes medical images acquired prior to the set reference date for deletion among the medical images stored in the storage unit, if a confirmation command regarding auto deletion is input.

14. The medical imaging apparatus according to claim 13, wherein the controller determines whether or not there is any medical image corresponding to a deletion exception condition among the medical images acquired prior to the set reference date for deletion.

15. The medical imaging apparatus according to claim 14, wherein the deletion exception condition includes at least one of whether or not medical images are sent to a picture archiving and communication system (PACS), whether or not medical images are printed, whether or not approval messages are received from the PACS, and whether or not a lock of medical images is set.

16. A medical image management method comprising:
storing medical images in a storage unit;
calculating a residual capacity of the storage unit and determining whether the calculated residual capacity is less than a predetermined reference value; and
displaying an auto deletion popup window receiving setup information regarding a reference date for deletion of the stored medical images, if the calculated residual capacity is determined to be less than the predetermined reference value.

17. The medical image management method according to claim 16, wherein the auto deletion popup window includes a plurality of period setup buttons corresponding to periods determining the reference date for deletion.

18. The medical image management method according to claim 17, further comprising:
if one of the plurality of period setup buttons is selected, determining the reference date for deletion based on the selected period setup button; and
displaying the determined reference date for deletion on the auto deletion popup window.

19. The medical image management method according to claim 18, wherein the auto deletion popup window includes information regarding the total storage capacity and current residual capacity of the storage unit.

20. The medical image management method according to claim 19, wherein the information regarding the total storage capacity and current residual capacity of the storage unit includes the maximum number of storable medical images or a numerical value displayed as a unit representing a storage capacity.

21. The medical image management method according to claim 20, wherein the auto deletion popup window includes information regarding the currently used capacity of the storage unit.

22. The medical image management method according to claim 21, wherein the information regarding the currently used capacity of the storage unit is displayed as a guide bar having a length proportional to the currently used capacity.

23. The medical image management method according to claim 22, wherein the guide bar is expressed in different colors according to currently used capacities.

24. The medical image management method according to claim 18, further comprising calculating a used capacity and a residual capacity after deletion of medical images being a target to be deleted among the medical images stored in the storage unit, if the reference date for deletion is set.

25. The medical image management method according to claim 24, further comprising displaying information regarding the used capacity and residual capacity after deletion on the auto deletion popup window.

26. The medical image management method according to claim 25, wherein the information regarding the used capacity after deletion is displayed as a guide bar having a length proportional to the used capacity after deletion.

27. The medical image management method according to claim 26, wherein the guide bar is expressed in different colors according to used capacities after deletion.

28. The medical image management method according to claim 24, further comprising deleting medical images acquired prior to the set reference date for deletion among the medical images stored in the storage unit, if a confirmation command regarding auto deletion is input.

29. The medical image management method according to claim 28, further comprising determining whether or not there is any medical image corresponding to a deletion exception condition among the medical images acquired prior to the set reference date for deletion.

30. The medical image management method according to claim 29, wherein the deletion exception condition includes at least one of whether or not medical images are sent to a picture archiving and communication system (PACS), whether or not medical images are printed, whether or not approval messages are received from the PACS, and whether or not a lock of medical images is set.

31. A non-transitory computer-readable recording medium storing a program to implement the method of claim 16.

32. An image management method comprising:
calculating a residual capacity of a storage unit;
determining whether the calculated residual capacity is less than a predetermined reference value;
selectively, based on the determination, receiving date-related information from a user in an auto deletion popup window; and
deleting images stored in the storage unit based on the received date-related information.

* * * * *